(12) United States Patent
Paredes Poblete et al.

(10) Patent No.: US 9,663,453 B2
(45) Date of Patent: May 30, 2017

(54) METABOLITES AND OXIMES WITH VASODILATOR AND HYPOTENSIVE ACTIVITY

(71) Applicant: Universidad de Antofagasta, Antofagasta (CL)

(72) Inventors: Adrian Guillermo Paredes Poblete, Antofagasta (CL); Glauco Segundo Morales Borcosque, Antofagasta (CL); Fredi Eduardo Cifuentes Jorquera, Antofagasta (CL)

(73) Assignee: UNIVERSIDAD DE ANTOFAGASTA, Antofagasta (CL)

( * ) Notice: Subject to any disclaimer, the term of this patent is extended or adjusted under 35 U.S.C. 154(b) by 0 days.

(21) Appl. No.: 14/876,084

(22) Filed: Oct. 6, 2015

(65) Prior Publication Data

US 2016/0130219 A1    May 12, 2016

Related U.S. Application Data

(60) Provisional application No. 62/072,677, filed on Oct. 30, 2014.

(51) Int. Cl.
*C07C 249/08*     (2006.01)
*C07D 307/79*     (2006.01)
*C07C 251/48*     (2006.01)
*C07C 249/14*     (2006.01)
*C07C 45/79*      (2006.01)

(52) U.S. Cl.
CPC ............ *C07C 249/08* (2013.01); *C07C 45/79* (2013.01); *C07C 249/14* (2013.01); *C07C 251/48* (2013.01); *C07D 307/79* (2013.01)

(58) Field of Classification Search
None
See application file for complete search history.

(56) References Cited

FOREIGN PATENT DOCUMENTS

WO         95/01157 A1     1/1995

OTHER PUBLICATIONS

Database CAPLUS in STN, Acc. No. 2005:246618, Guzman et al., Journal of the Chilean Chemical Society (2005), 50(1), pp. 383-387 (abstract).*

* cited by examiner

*Primary Examiner* — Brian J Davis
(74) *Attorney, Agent, or Firm* — Lucas & Mercanti, LLP

(57) ABSTRACT

Semi-synthetic oximes derived from metabolites extracted from medicinal plants, *Senecio nutans* and *Xenophyllum poposum*, the method of preparation thereof and their use as agents with vasodilator and hypotensive effects are provided.

6 Claims, 32 Drawing Sheets

METABOLITES AND OXIMES WITH VASODILATOR AND HYPOTENSIVE ACTIVITY

CROSS REFERENCE TO RELATED APPLICATION

This application claims priority from U.S. Provisional Application No. 62/072,677 filed on Oct. 30, 2014, application which is incorporated herein by reference.

FIELD OF INVENTION

The present invention relates to pharmaceutical industry. In particular, the present invention is referring to two semi-synthetic oximes derived from metabolites extracted from medicinal plants, Senecio nutans and Xenophyllum poposum, the method of preparation thereof and their use as agents with vasodilator and hypotensive effects.

BACKGROUND OF THE INVENTION

US Patent Application 2009234023 describes substituted hydroxyacetophenone derivatives having antiproliferative and antimicrobial properties, pharmaceutical compositions containing them, as well as a method of preparation. Additionally, hydroxyacetophenone derivatives according to what disclosed therein serve as organic intermediates for the preparation of biologically active compounds. Patent Application WO1995001157A1 describes methods and photoprotective compositions comprising a compound of structure (I) and a pharmaceutically acceptable topical carrier.

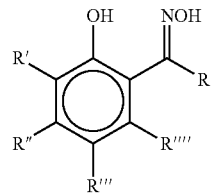

This application though disclosing the main structure of one of the oxime derivatives, does not teach any of the compounds disclosed herein, or disclose the process of preparation of any of them from metabolites extracted from medicinal plants, S. nutans and X. poposum, much less use as vasodilators or hypotensive agents.

DEFINITIONS OF ABBREVIATIONS

Ach Acetylcholine
DEPT Distortionless Enhanced Polarization Transfer
DMSO Dimethylsulfoxide
E− Aortic rings without endothelium.
E+ Aortic ring with intact endothelium
$EC_{50}$ Effective Concentration 50.
$E_{max}$ Maximum effect.
PHE Phenylephrine
HMBC Heteronuclear Multiple Bond Correlation
HMQC Heteronuclear Multiple-Quantum Correlation
HSQC Heteronuclear Single Quantum Correlatión
IR Infrared.
$Kg_{wt}$ Kilograms by body weight.
mmHg: millimeters of Mercury
NPS Sodium nitroprusside
p.f. Melting Point
P.A. Blood Pressure
P.A.M. Blood Pressure Media
Prop Propranolol
RMN $^{13}$C Carbon 13 Nuclear Magnetic Resonance
RMN $^{1}$H Proton Nuclear Magnetic Resonance

BRIEF DESCRIPTION OF THE INVENTION

The present invention describes the method of preparation of semi-synthetic oximes derived from metabolites extracted from medicinal plants, Senecio nutans and Xenophyllum poposum. These oximes have vasodilating and hypotensive properties being an alternative for treating arterial hypertension.

Specifically, the present invention describes a method of preparation of semi-synthetic oximes (1) and (2) derived from the metabolites (A) and (B), obtained from medicinal extracts from S. nutans and X. poposum plants.

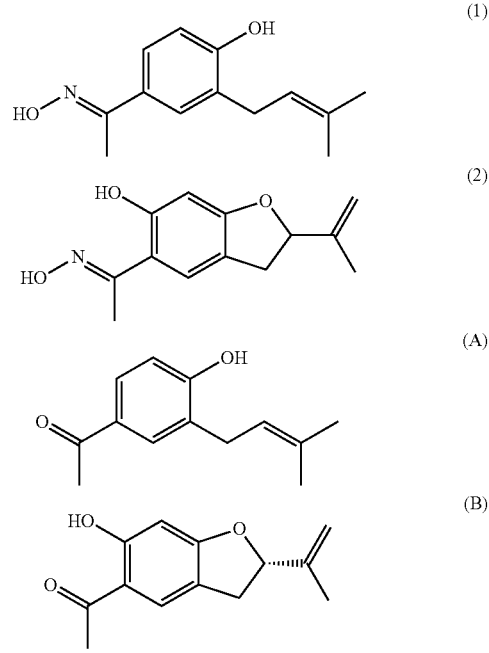

DESCRIPTION OF THE INVENTION

A method of preparing semi-synthetic oximes comprising:

a) applying an extract of *Senecio nutans* and/or *Xenophyllum poposum* plants to column chromatography and thin layer chromatography, to obtain a metabolite of formula:

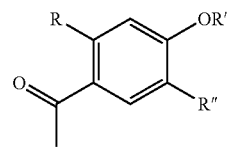

wherein R corresponds to H, OH or methyl; R' and R" corresponds to H, methyl, propyl, propylene, 3-methylbutyl-2-ene, or R' y R" together form a system derived from dihydrobenzofuran.

b) heating under reflux between 100 mg to 400 mg of the starting metabolite with a mixture of from 30 to 250 mg of hydroxylamine hydrochloride dissolved in 5 mL of ethanol and from 150-400 μL of pyridine for 18-38 hours at 40° C. to 60° C.;

c) separating the organic phase from the reaction mixture by liquid-liquid extraction using an organic solvent such as dichloromethane, chloroform, ethyl acetate or ethyl ether;

d) concentrating the organic phase on a rotary evaporator;

e) purifying the oxime by silica gel column chromatography, wherein the progress of the column is monitored by thin layer chromatography.

The metabolites obtained in step (a) are (A) and (B) which formulas are:

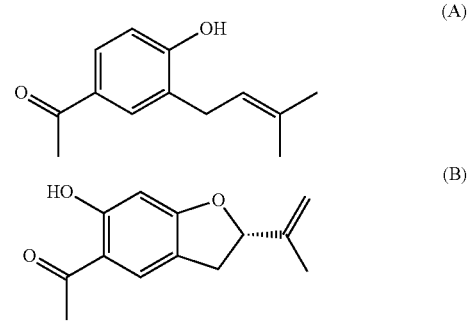

In step (c) for the preparation of semi-synthetic oximes, dichloromethane is mainly used as solvent.

Semi-synthetic oximes derived from metabolites obtained from medicinal plant extracts as described above have the following formula:

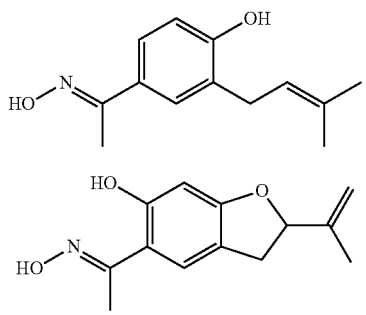

(1)

(2)

The semi-synthetic oximes (1) and (2) are useful to prepare a medicament useful as vasodilator or hypotensive agent.

Said medicament is useful as vasodilator, in conditions such as hypertension treatment, some no neurological migraines or headaches, varices treatment, mild cases of hypothermia, as coadjuvant in some drug abuse poisoning such as by cocaine, or pressure disorders not associated with acute arterial hypertension.

EXAMPLES

Example 1

The processes for identifying metabolites and preparation of semi-synthetic oximes are as follows:

Identification of Metabolite (A) (4-hydroxy-3-(isopenten-2-yl)-acetophenone)

Metabolite (A) isolated from *S. nutans* and *X. poposum* is crystallized in toluene as white crystals with a melting point of 90-92° C. and molecular weight of 204 g/mole assignable to $C_{13}H_{16}O_2$.

Figure 15:
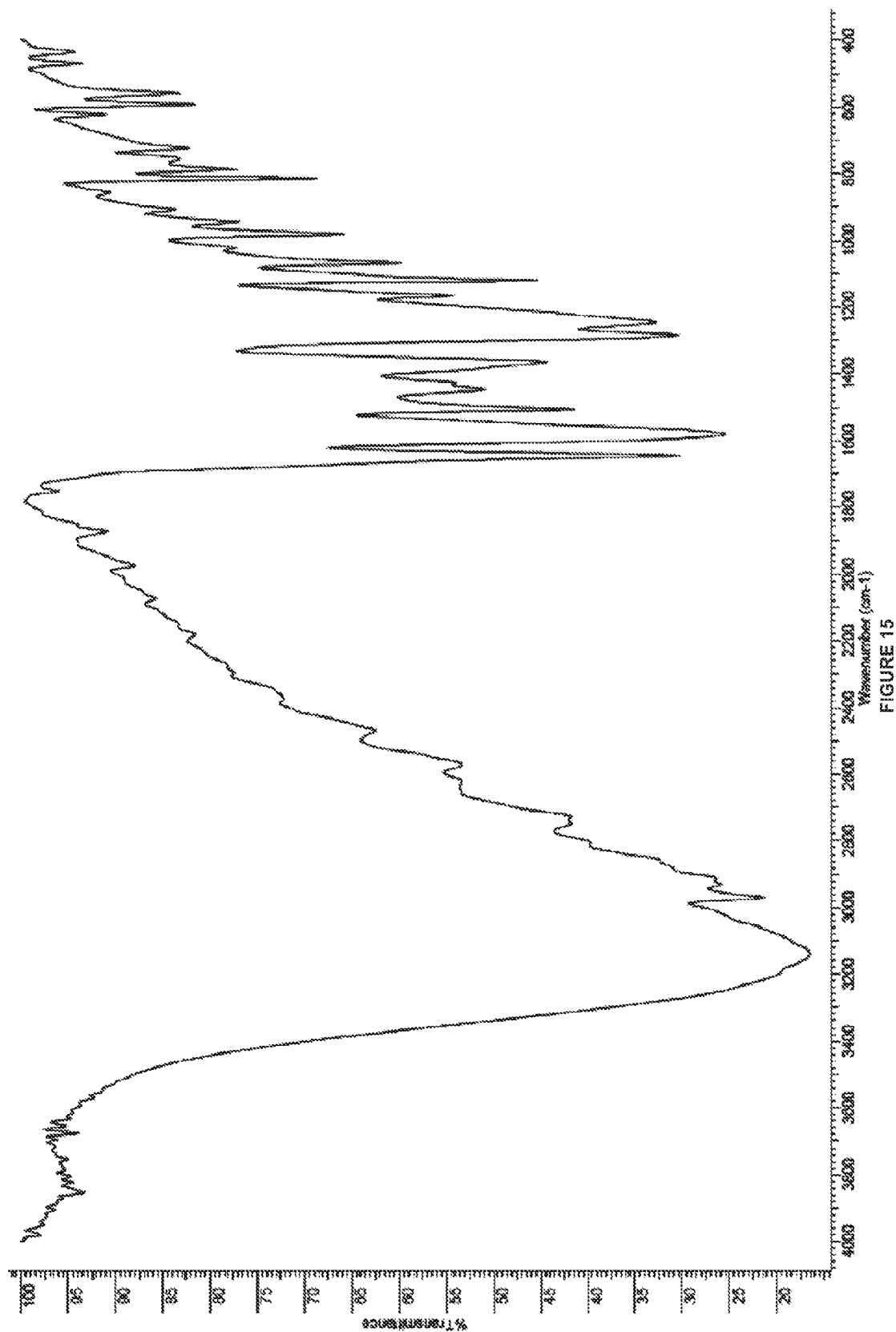
FIG. 15 shows an IR spectrum of 4-hydroxy-3-(isopenten-2-yl)-acetophenone.
Figure 16:
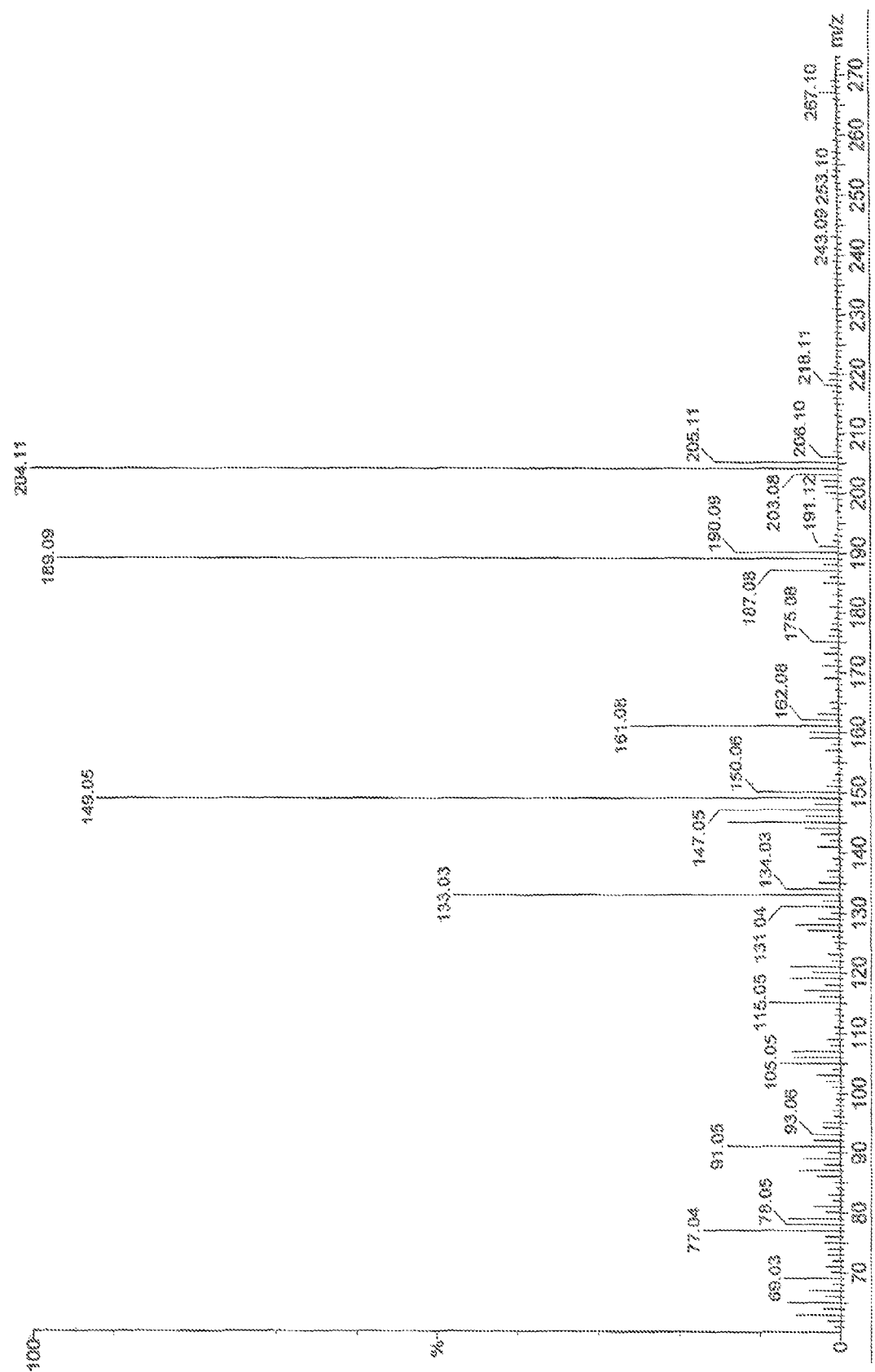
FIG. 16 shows a mass spectrum of 4-hydroxy-3-(isopenten-2-yl)-acetophenone.

IR spectrum, as shown in FIG. 15, shows low intensity bands between 1750-2000 $cm^{-1}$ and 1350-1550 $cm^{-1}$ assignable to the presence of benzene ring, a broadband between 3000-3500 $cm^{-1}$ associated with presence of hydroxyl group and an intense band at 1645 $cm^{-1}$ corresponding to an aromatic carbonyl group.

Figure 10:
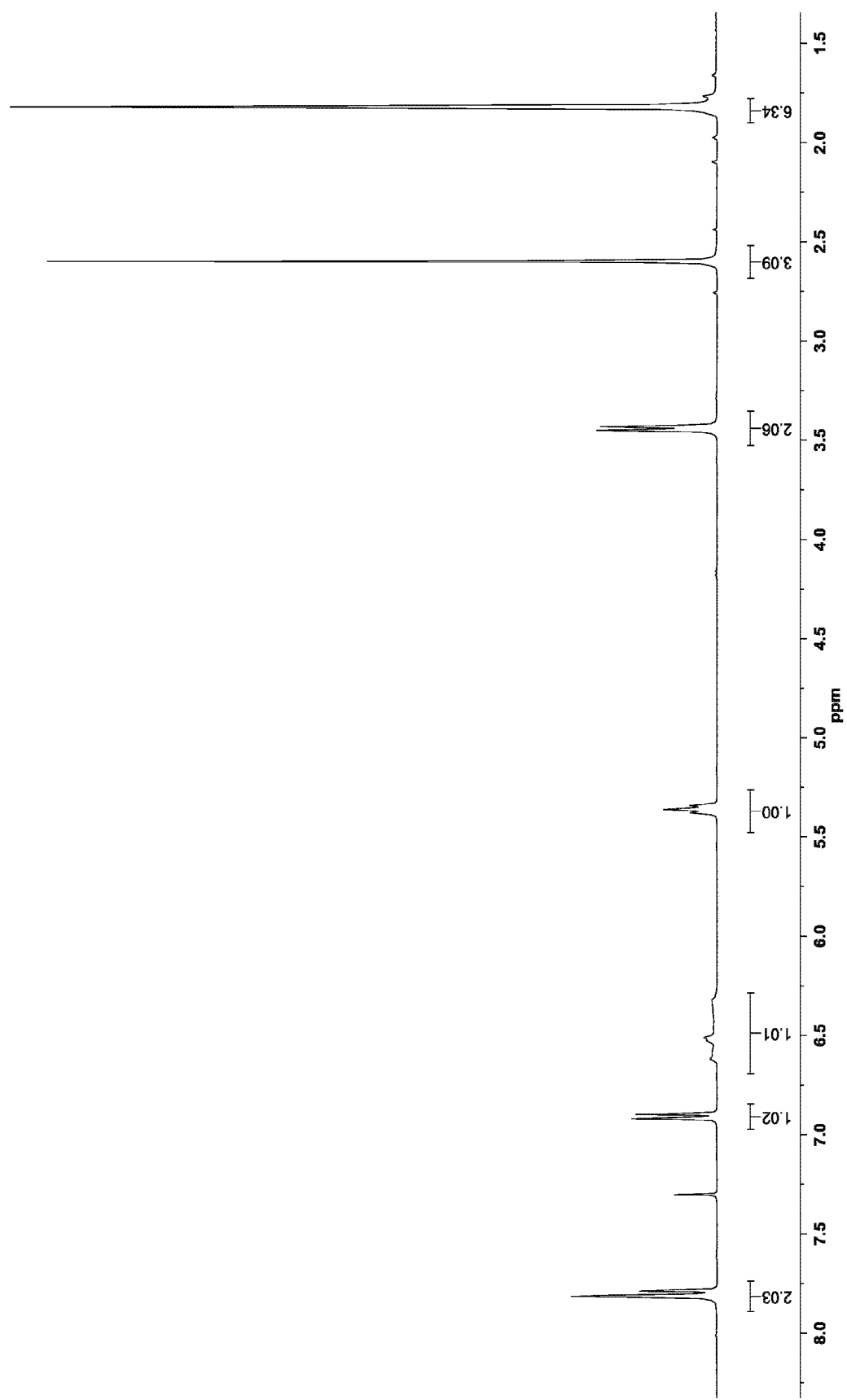
FIG. 10 shows a $^1$H-NMR spectrum of 4-hydroxy-3-(isopenten-2-yl)-acetophenone.
Figure 11:
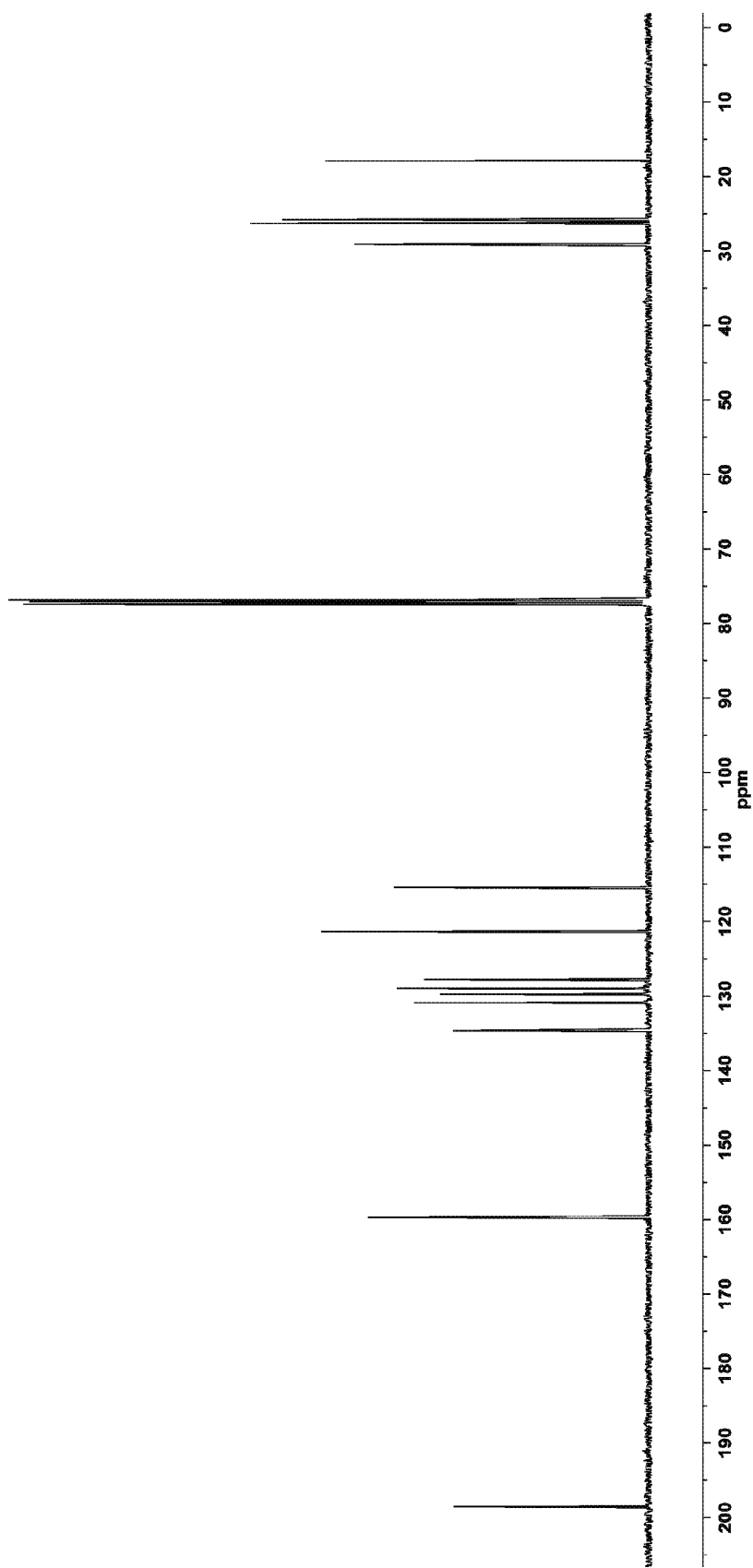
FIG. 11 shows a $^{13}$C-NMR spectrum of 4-hydroxy-3-(isopenten-2-yl)-acetophenone.
Figure 12:
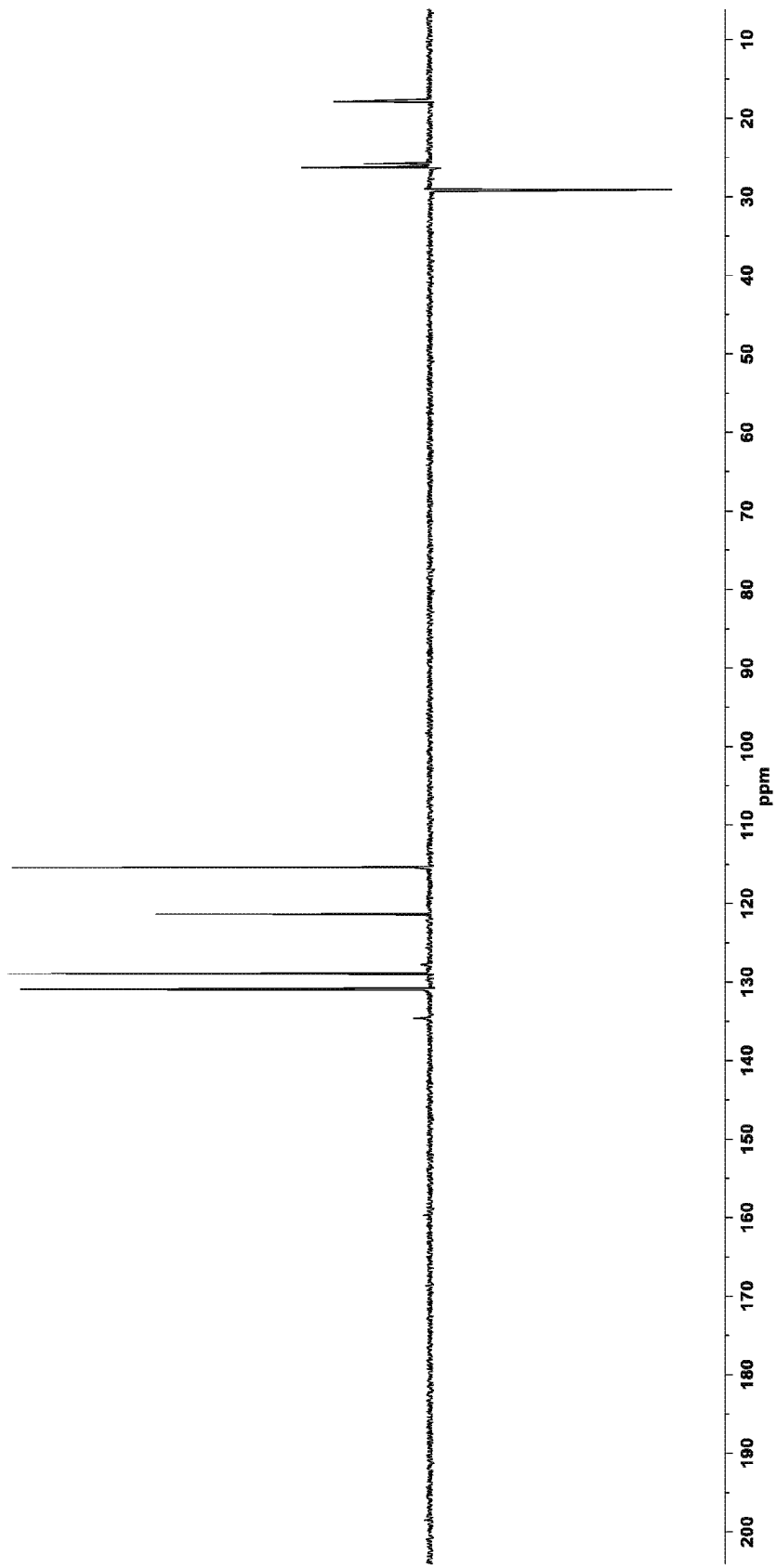
FIG. 12 shows a DEPT spectrum of 4-hydroxy-3-(isopenten-2-yl)-acetophenone.

$^1$H-NMR spectrum, as shown in FIG. 10, shows signals assignable to 16 hydrogen atoms; and $^{13}$C-NMR spectrum, as shown in FIG. 11, shows signals assignable to 13 carbon atoms. Chemical shifts and DEPT spectrum showned in FIG. 12 revealed the presence of three $CH_3$ groups and an α $CH_2$ group to the aromatic ring, three aromatic CH groups, an olefinic CH group, and 5 $sp^2$-type quaternary carbons. A methyl group is inherent to $CH_3CO$ group, the two remaining methyl are vinyl methyl.

Spectroscopic analysis shows that structure of the metabolite (A) corresponds to 4-hydroxy-3-(isopenten-2-yl)-acetophenone.

HMQC spectrum shows that methyl vinyl protons that resonate at δ 1.82 ppm are bonded with the carbon atoms at δ 17.91 ppm (C-11) and at δ 25.80 ppm (C-10), olefinic proton resonating at δ 5.36 ppm is connected with $sp^2$ C at δ 121.33 ppm (C-8). The α $CH_2$ to aromatic ring resonates at δ 3.44 ppm (2H, d, J=8.0 Hz) and is bonded to C at δ 29.11 ppm (C-7).

Figure 13:
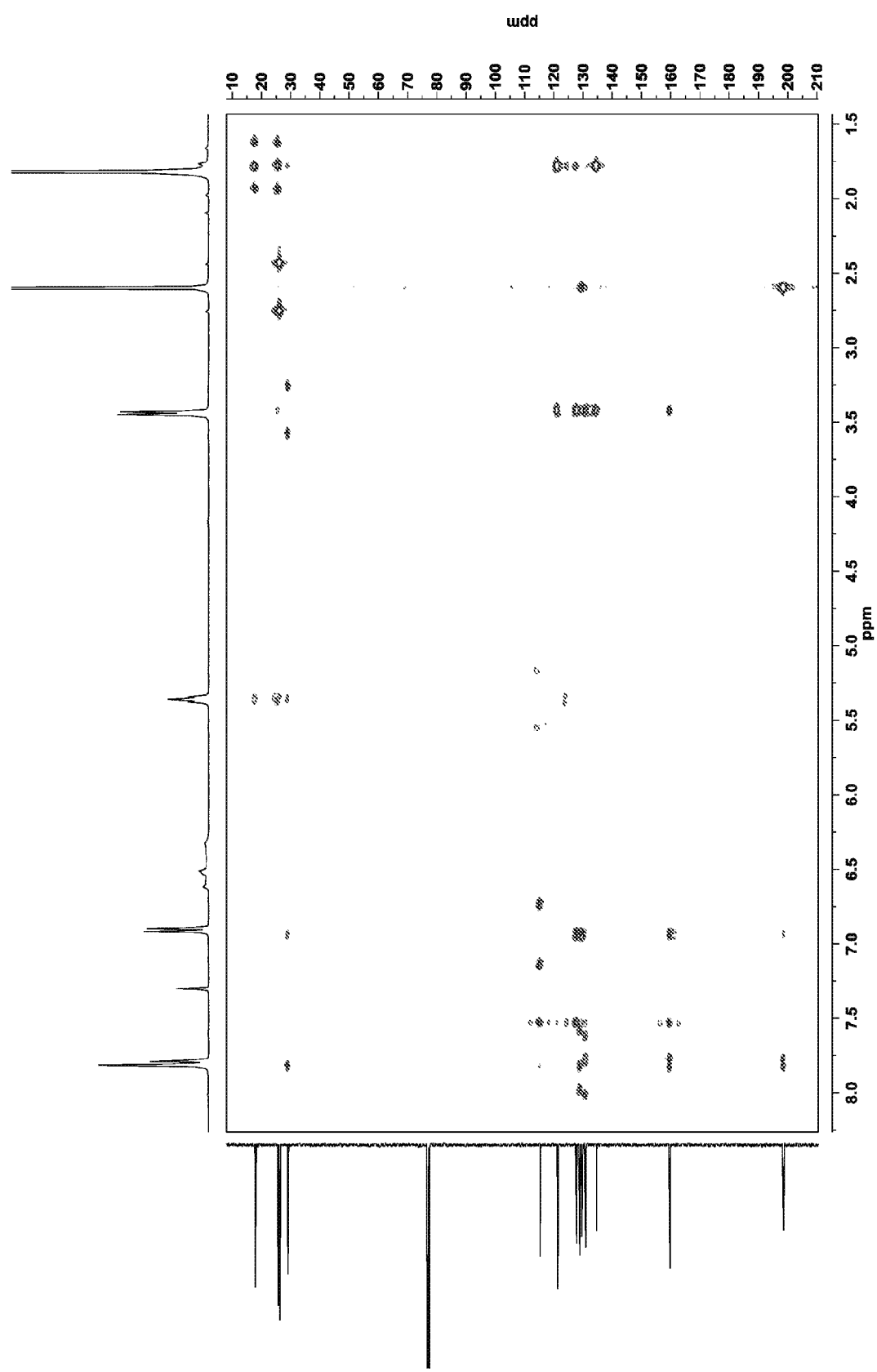
FIG. 13 shows a HMBC spectrum of 4-hydroxy-3-(isopenten-2-yl)-acetophenone.
Figure 14:
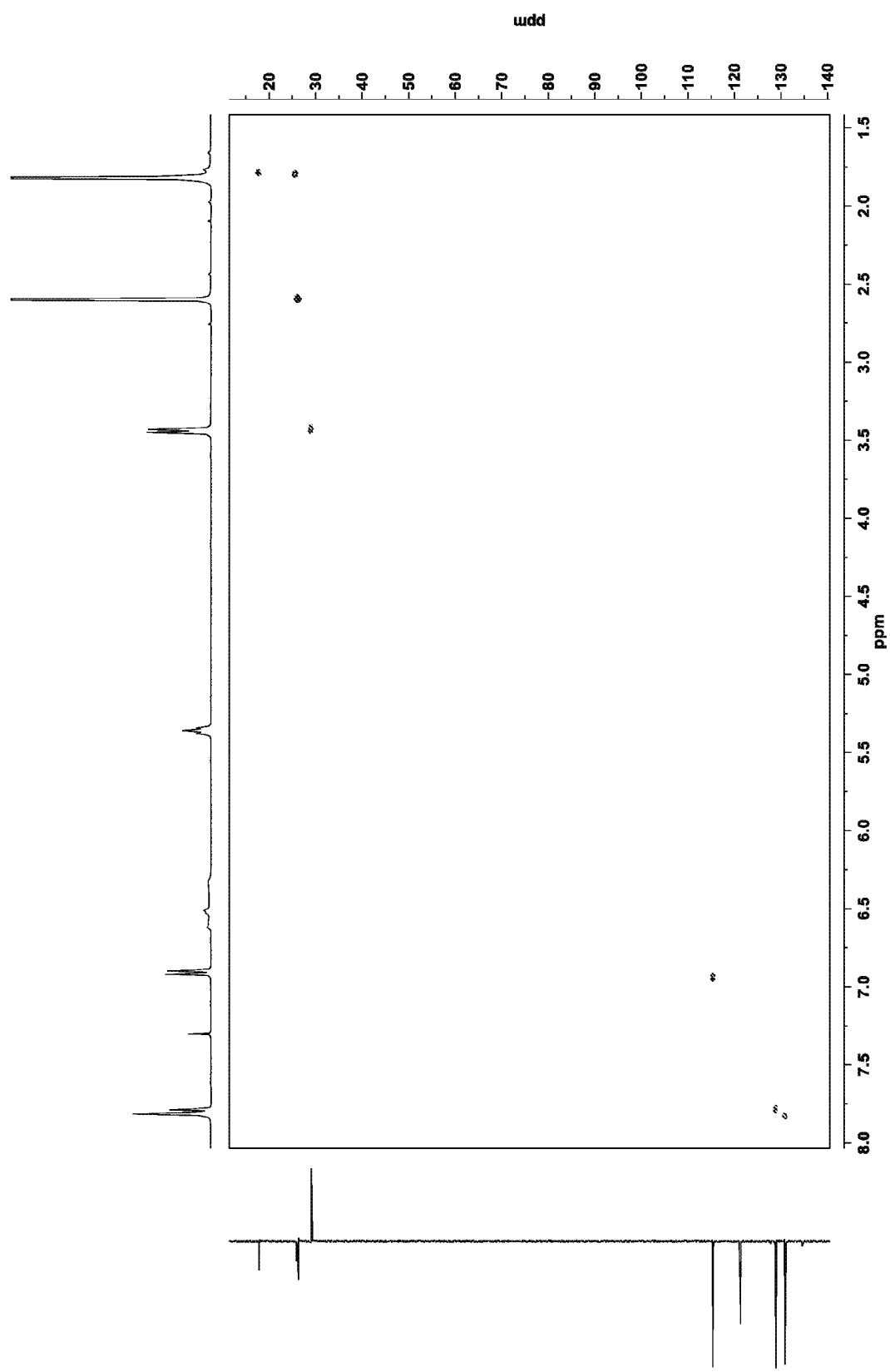
FIG. 14 shows a HMQC spectrum of 4-hydroxy-3-(isopenten-2-yl)-acetophenone.

Coupling patterns deduced by HMBC spectrum FIG. 13, of 4-hydroxy-3-(isopenten-2-yl)acetophenone are shown in Table 1 and in the following Connectivity Scheme:

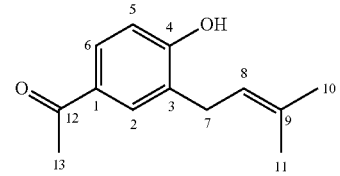

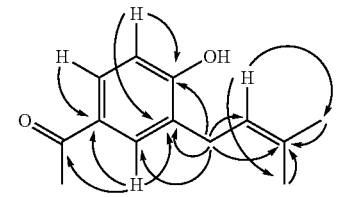

TABLE 1

Connectivity for 4-hydroxy-3-(isopenten-2-yl)acetophenone deduced by HMBC

| Position | $\delta_H$ (ppm) | Coupling Patterns |
|---|---|---|
| 2 | 7.79 | C1, C3 and C12 |
| 5 | 6.91 | C3 and C4 |
| 6 | 7.80 | C1 |
| 7 | 3.44 | C2, C3, C4, C8 and C9 |
| 8 | 5.36 | C10 and C11 |
| 10 | 1.82 | C9 |
| 11 | 1.82 | C9 |
| OH | 6.57 | C3, C4 and C5 |

Identification of Metabolite (B) (6-hydroxy-2-isopropenyl-5-acetyl-2,3-dihydrobenzofuran)

Metabolite (B) isolated from *S. nutans* and *X. poposum* is crystallized in petroleum ether as colorless crystals with a melting point of 68-70° C. and molecular weight $M^+$ 218 assignable to $C_{13}H_{14}O_3$.

Figure 22:
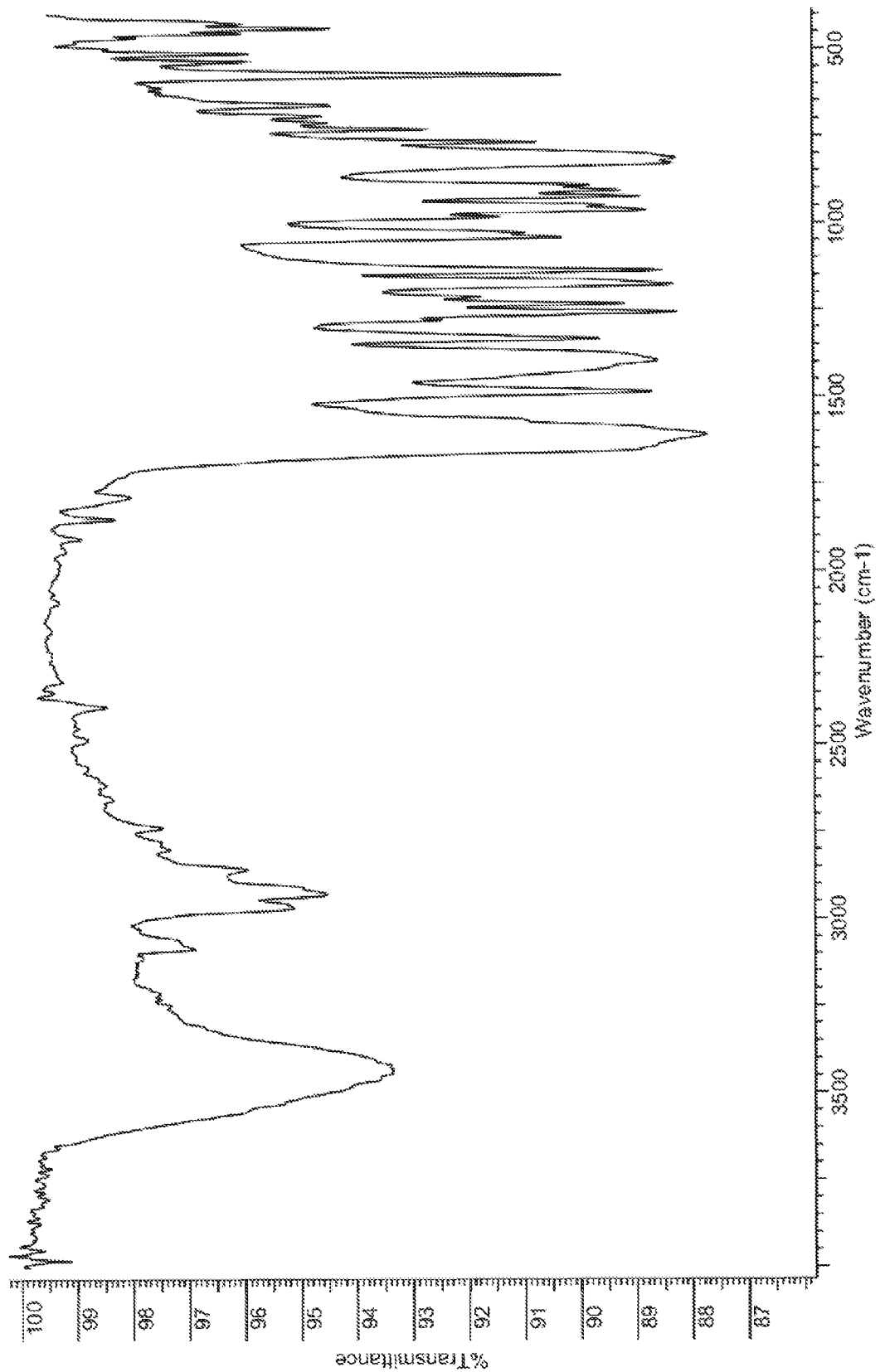
FIG. 22 shows a IR spectrum of 6-hydroxy-2-isopropenyl-5-Acetyl-2,3-dihydrobenzofuran.
Figure 23:
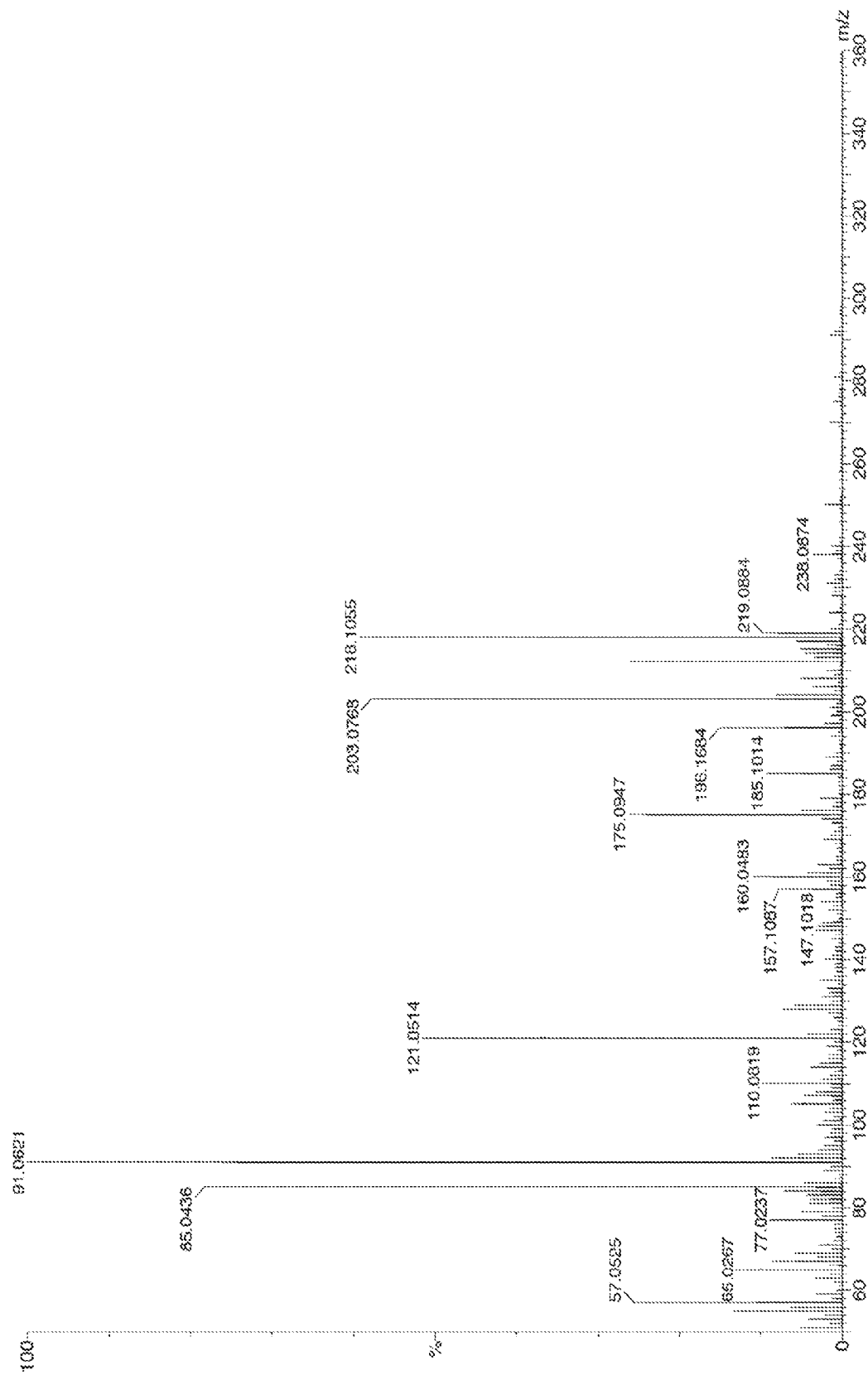
FIG. 23 shows a mass spectrum of 6-hydroxy-2-isopropenyl-5-Acety-2,3-dihydrobenzofuran.

IR spectrum of FIG. 22 shows a broad band between 3250 and 3500 $cm^{-1}$ associated to the presence of an OH group, a number of lower intensity bands between 1700-1900 $cm^{-1}$ and 1300-1500 $cm^{-1}$ attributable to the presence of an aromatic ring and an absorption band at 1640 $cm^{-1}$ corresponding to a carbonyl group of aromatic ketone.

Figure 17:
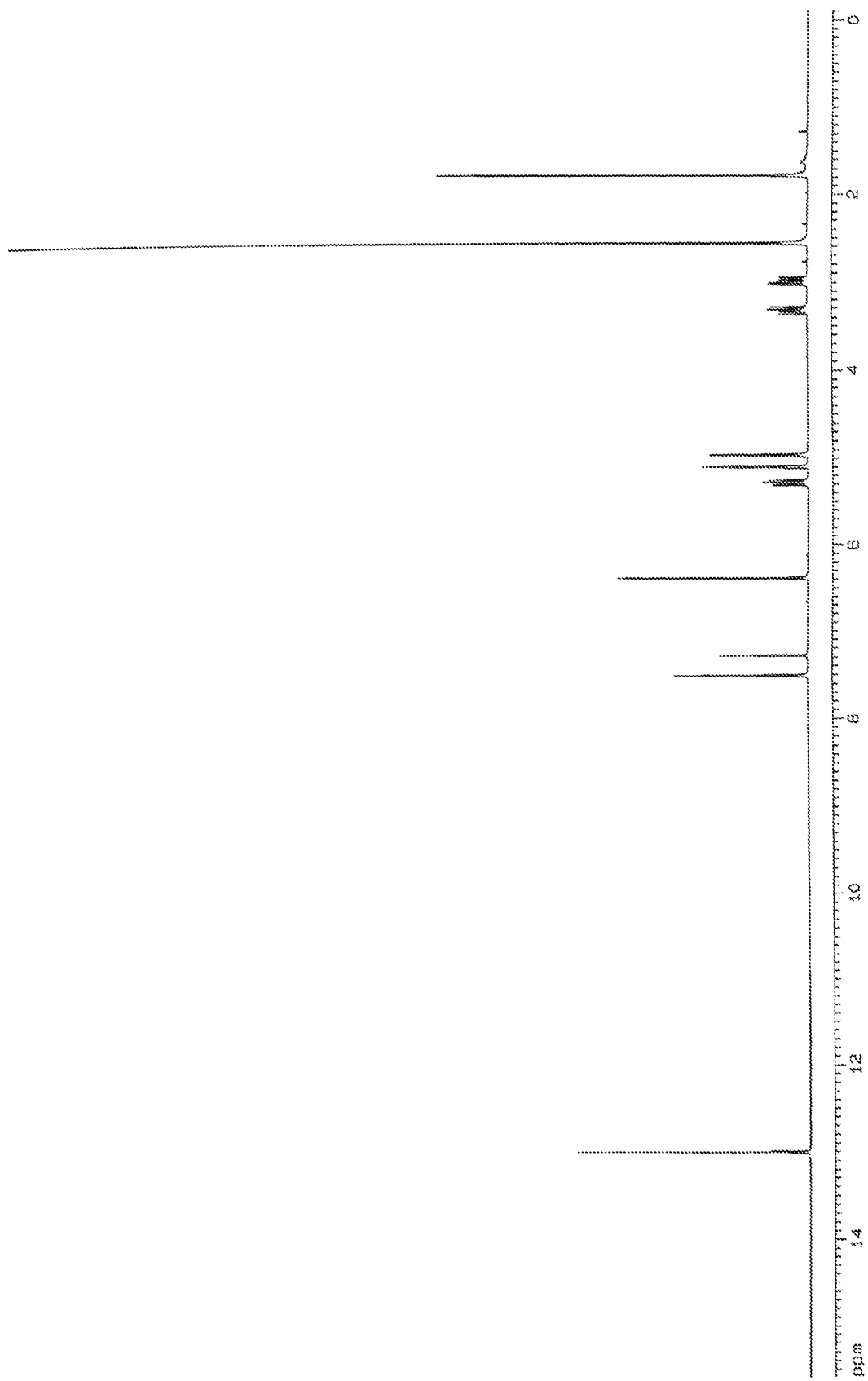
FIG. 17 shows a $^1$H-NMR spectrum of 6-hydroxy-2-isopropenyl-5-Acetyl-2,3-dihydrobenzofuran.
Figure 18:
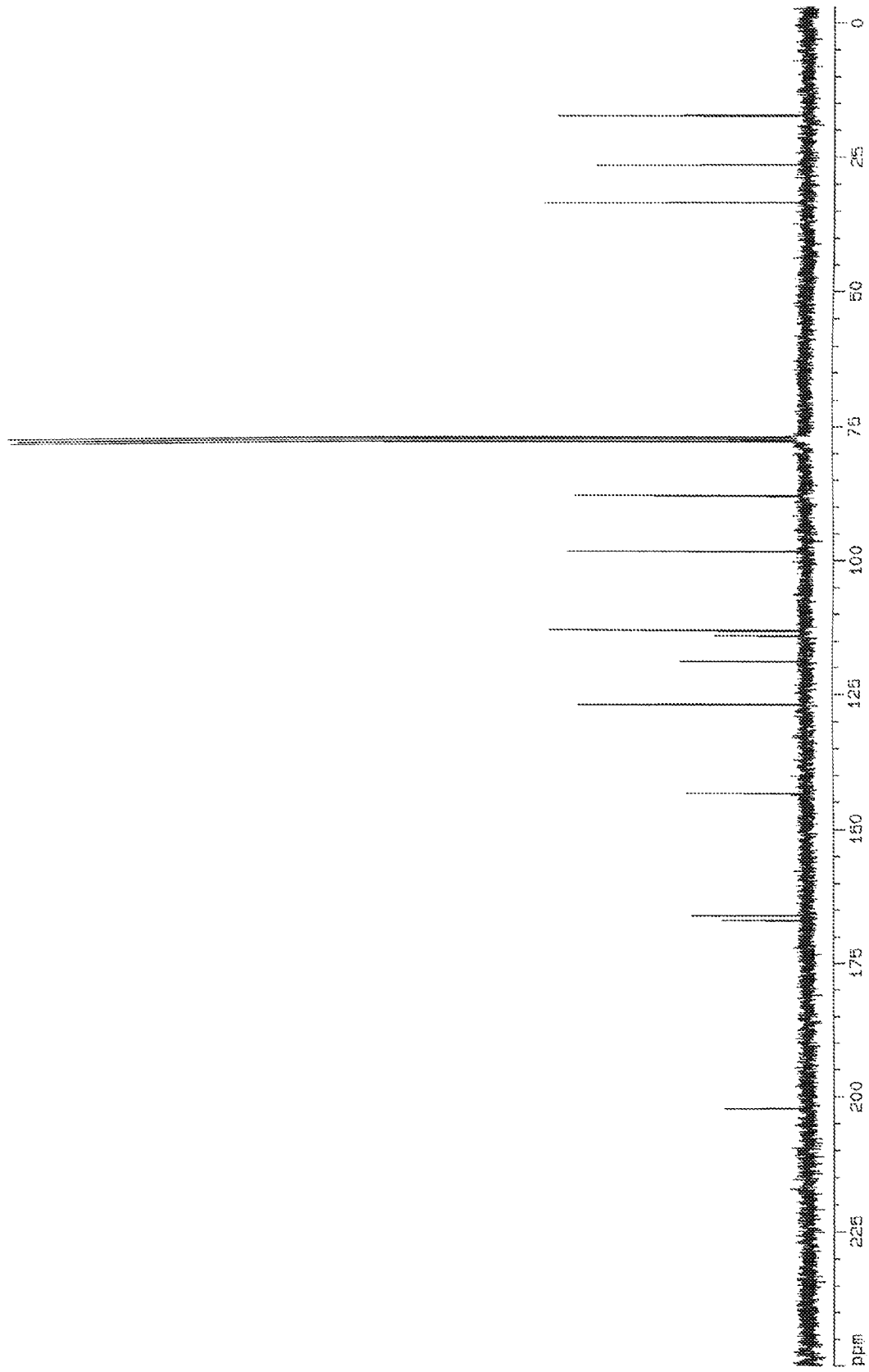
FIG. 18 shows a $^{13}$C-NMR spectrum of 6-hydroxy-2-isopropenyl-5-Acetyl-2,3-dihydrobenzofuran.
Figure 19:
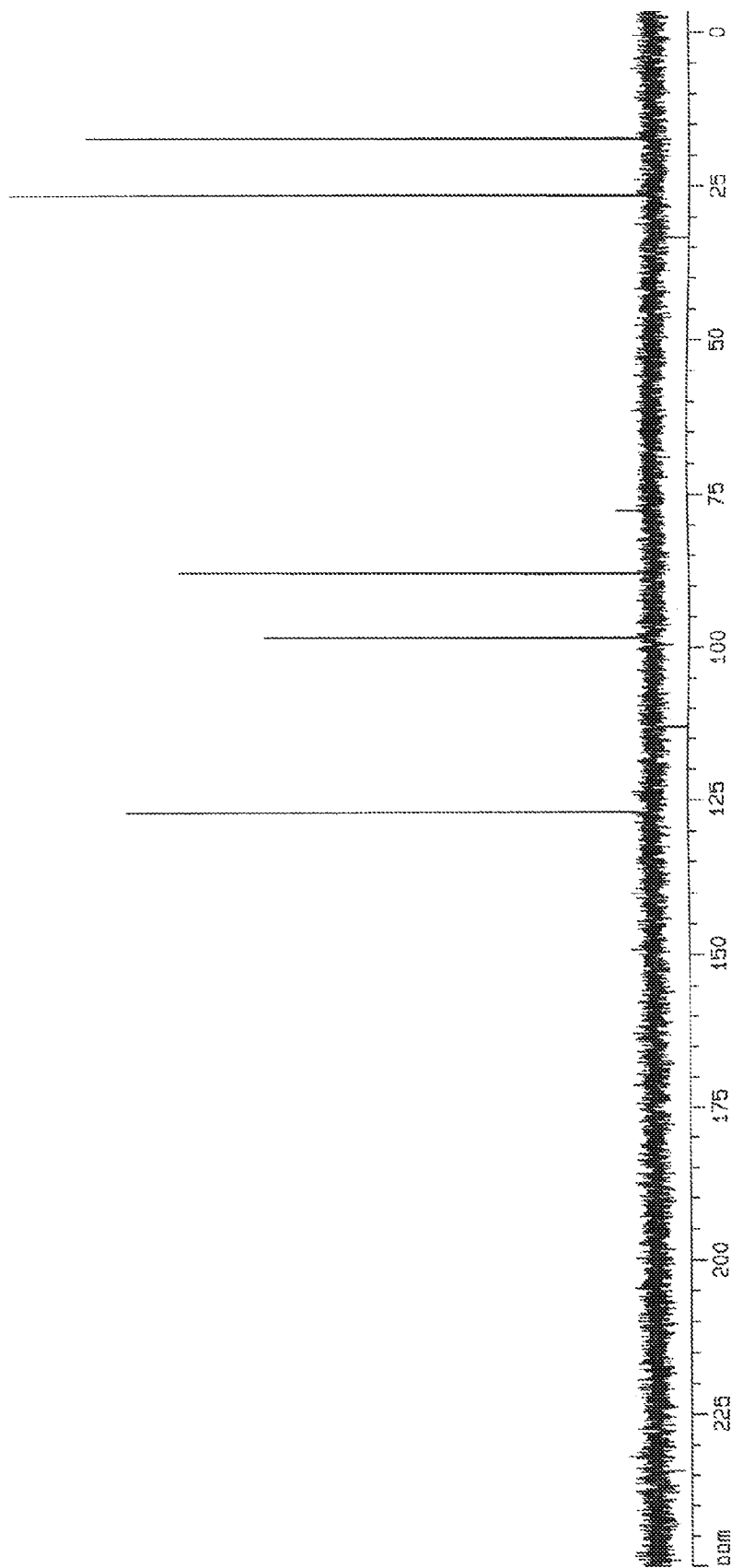
FIG. 19 shows a DEPT spectrum of 6-hydroxy-2-isopropenyl-5-Acetyl-2,3-dihydrobenzofuran.

$^1$H-NMR spectrum from FIG. 17 shows signals assignable to 14 hydrogen atoms, and $^{13}$C-NMR spectrum of FIG. 18 shows signals assignable to 13 carbon atoms, respectively. Chemical shifts and DEPT spectrum of FIG. 19 clearly indicate the presence of two $CH_3$, an α $CH_2$ to the aromatic ring, a $sp^2$-type $CH_2$, two aromatic OH, a $sp^3$ CH and six $sp^2$-type quaternary carbons.

Spectroscopic information of metabolite (B) is consistent with the one described for 6-hydroxy-2-isopropenyl-5-acetyl-2,3-dihydrobenzofuran (dehydroeuparin).

Figure 21:
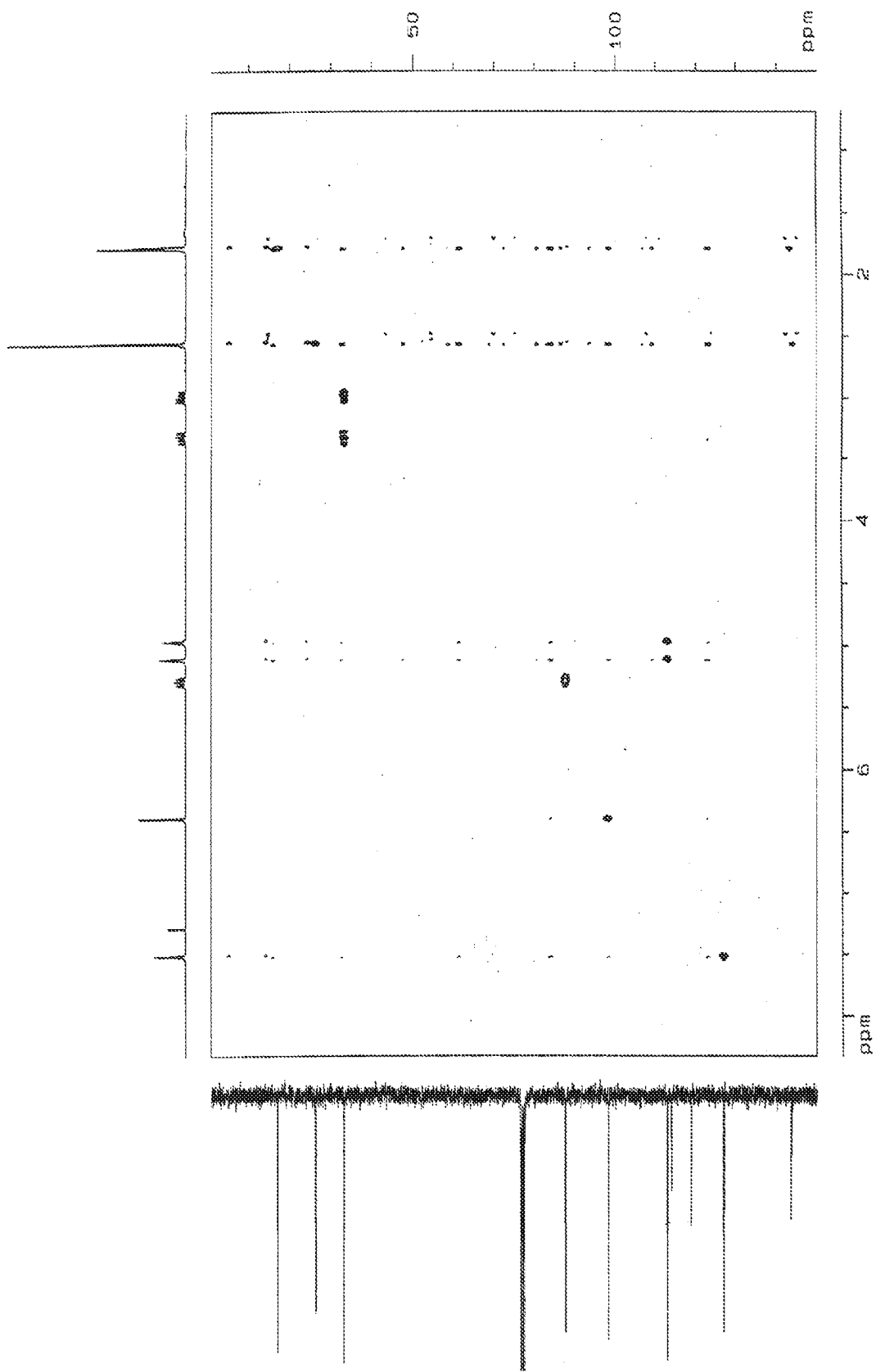
FIG. 21 shows a HMQC spectrum of 6-hydroxy-2-isopropenyl-5-Acetyl-2,3-dihydrobenzofuran in CDCl$_3$.

HMQC spectrum from FIG. 21 allow us to establish the following relationships, the proton that resonates at δ 6.38 ppm is bonded to the carbon atom that resonates at δ 98.33 ppm assignable to C-5, the proton at δ 7.75 with a carbon that resonates at δ 126.91 ppm (C-2), the proton at δ 5.28 with a carbon at δ 87.85 ppm (C-8). While the $sp^2$ C that resonates at δ 113.00 ppm (C-10) is bonded to protons that resonate at δ 5.10 and δ 4.95 ppm respectively.

Figure 20:
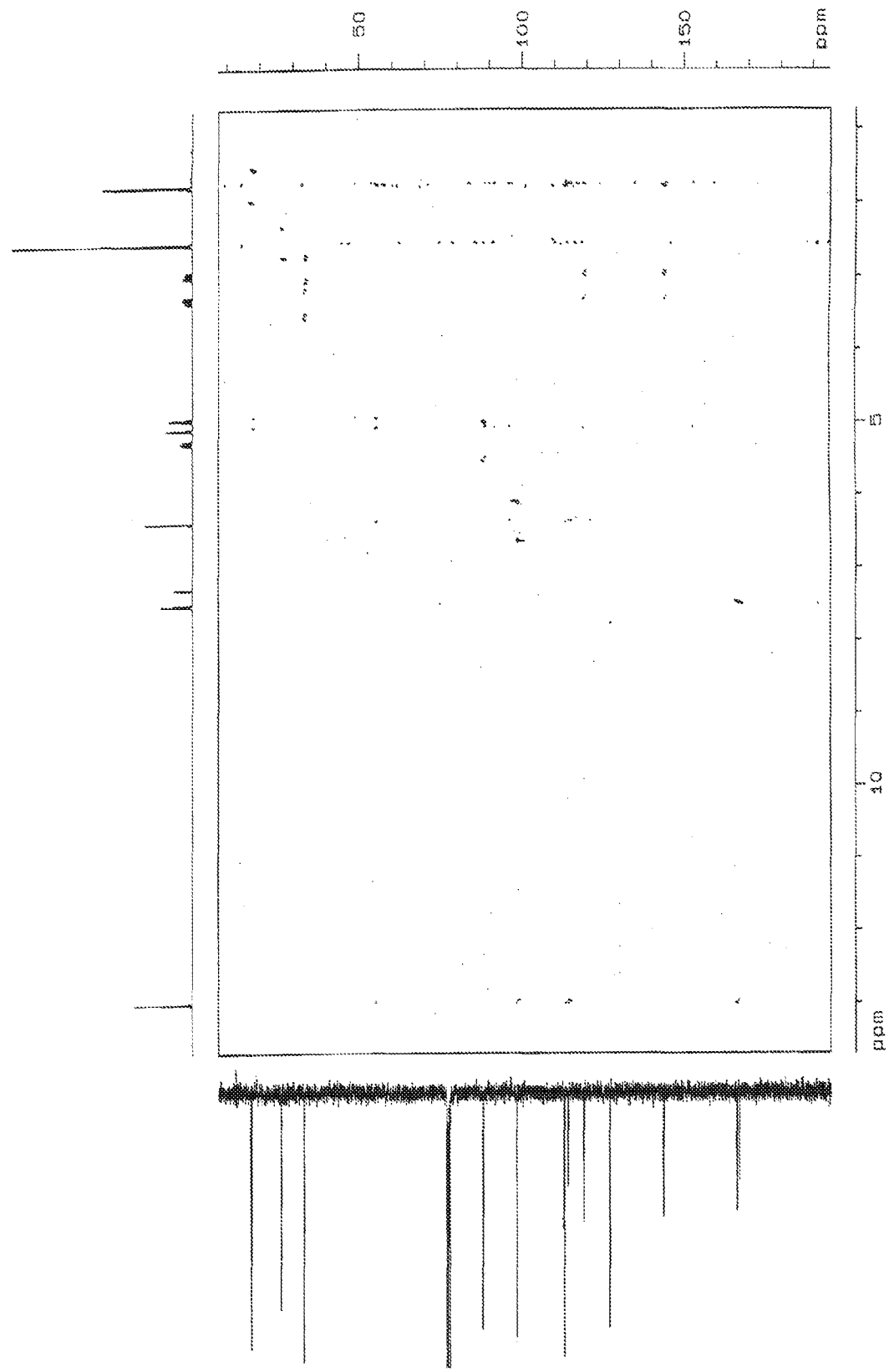
FIG. 20 shows a HMBC spectrum of 6-hydroxy-2-isopropenyl-5-Acetyl-2,3-dihydrobenzofuran.

Coupling patterns deduced by HMBC spectrum FIG. 20, of 6-hydroxy-2-isopropenyl-5-acetyl-2,3-dihydrobenzofura are shown in Table 2 and in the following Connectivity Scheme:

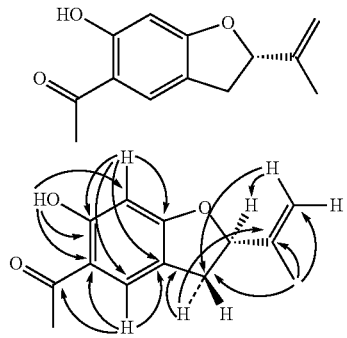

TABLE 2

Connectivity for 6-hydroxy-2-isopropenyl-5-acetyl-2,3-dihydrobenzofuran deduced by HMBC

| Position | $\delta_H$ (ppm) | Coupling Patterns |
| --- | --- | --- |
| 2 | 7.79 | C1, C3 and C12 |
| 5 | 6.38 | C2, C3, C4 and C5 |
| 7 | 3.32 | C3 and C9 |
| 10 | 5.10 | C7 and C8 |
| 11 | 1.78 | C7, C9 and C10 |
| OH | 12.99 | C1, C5 and C6 |

Example 2

Method of Preparing Semi-Synthetic Oximes (1) and (2)

Oximes of the compounds 4-hydroxy-3-(isopenten-2-yl) acetophenone (1) and 6-hydroxy-2-isopropenyl-5-acetyl-2,3-dihydrobenzofuran (2) were prepared as taught below:

I.—Preparation of oxime (1) from metabolite (A)

a) 200 mg of 4-hydroxy-3-(isopenten-2-yl)acetophenone were mixed with a mixture of 90 mg of hydroxylamine hydrochloride dissolved in 5 mL of ethanol and 300 uL of pyridine by heating under reflux for 24 h;
b) organic phase is removed from the mixture by liquid-liquid extraction using dichloromethane as solvent;
c) organic phase was concentrated on a rotary evaporator and applied to silica gel column chromatography for product purification.

II.—Preparation of oxime (2) from metabolite (B)

a) 200 mg of 6-hydroxy-2-isopropenyl-5-acetyl-2,3-dihydrobenzofuran were mixed with a mixture of 100 mg of hydroxylamine hydrochloride dissolved in 5 mL of ethanol and 300 uL of pyridine by heating under reflux for 24 h;
b) organic phase is removed from the mixture by liquid-liquid extraction using dichloromethane as solvent;
c) organic phase was concentrated on a rotary evaporator and applied to silica gel column chromatography for product purification.

Elution of each column in both cases was monitored by thin layer chromatography. Thus, the corresponding oximes (1) and (2) were obtained whose yields are shown in Table 3.

TABLE 3

Yields of oxime preparation from isolated compounds.

| | Mass of Compound (mg) | Reaction product mass (READY) (mg) | Obtained oxime % Yield |
| --- | --- | --- | --- |
| Metabolite (A) | 214 | 188 | 82% |
| Metabolite (B) | 226 | 185 | 77% |

Each product was characterized by $^1$H-NMR, $^{13}$C-NMR spectroscopy, mono and two-dimensional, IR spectroscopy; and MS confirmed the formation of the expected products.

Reaction schemes for preparation of the oximes derived from the Metabolites (A) and (B) are taught below, respectively:

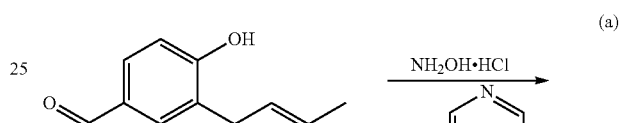

(a)

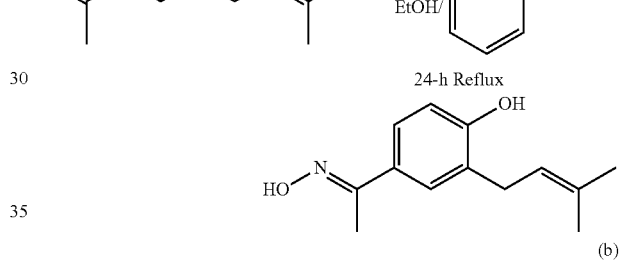

(b)

Oxime of Metabolite (A) (4-hydroxy-3-(isopenten-2-yl)-acetophenoxime)

4-hydroxy-3-(isopenten-2-yl)-acetophenoxime crystallized in dichloromethane as green crystal, with a melting point of 118-120° C. and a molecular weight of 219, which is attributable to $C_{13}H_{17}NO_2$.

Figure 28:
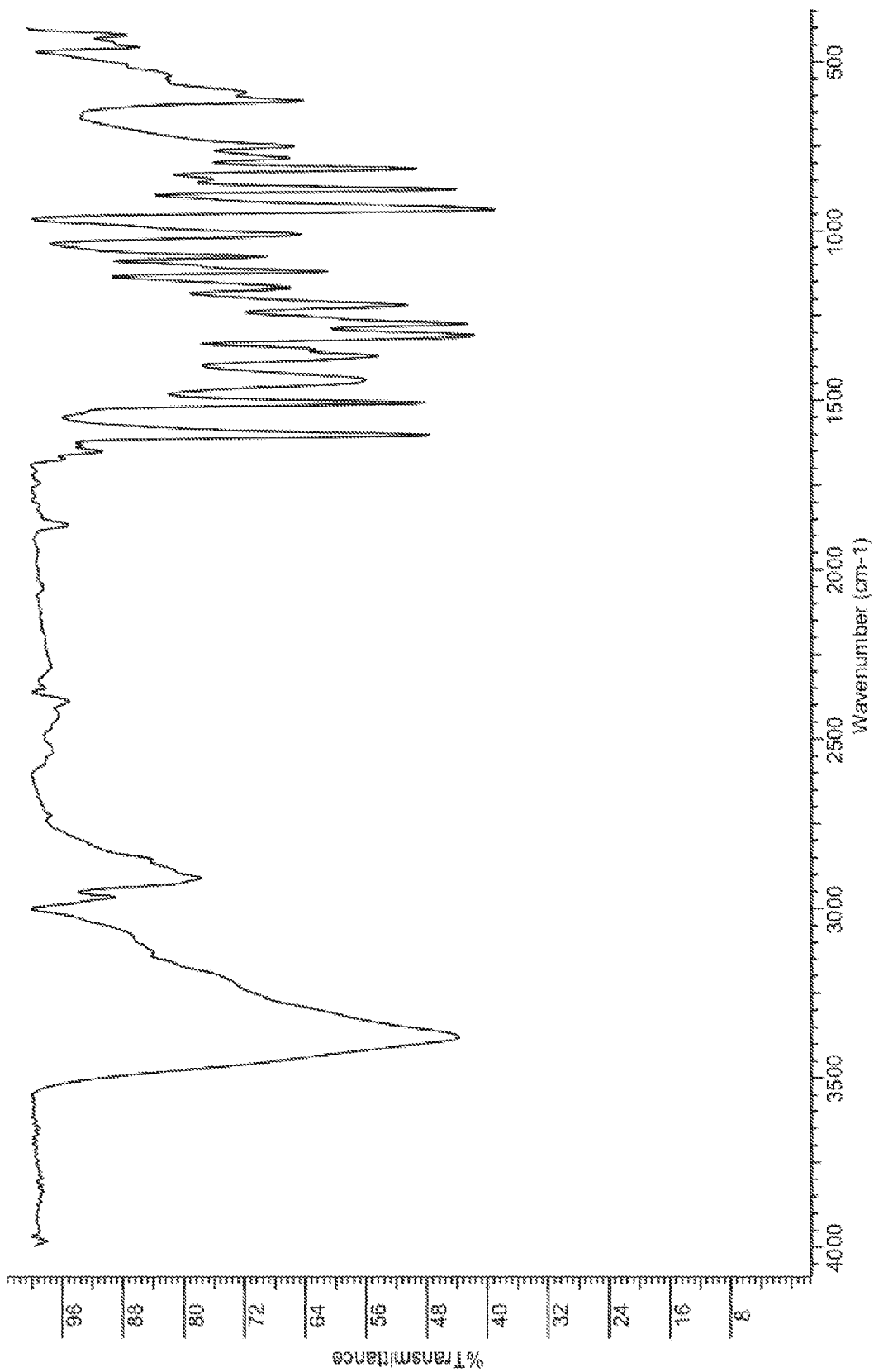
FIG. 28 shows an IR spectrum of 4-hydroxy-3-(isopenten-2-yl)-acetophenoxime.
Figure 29:
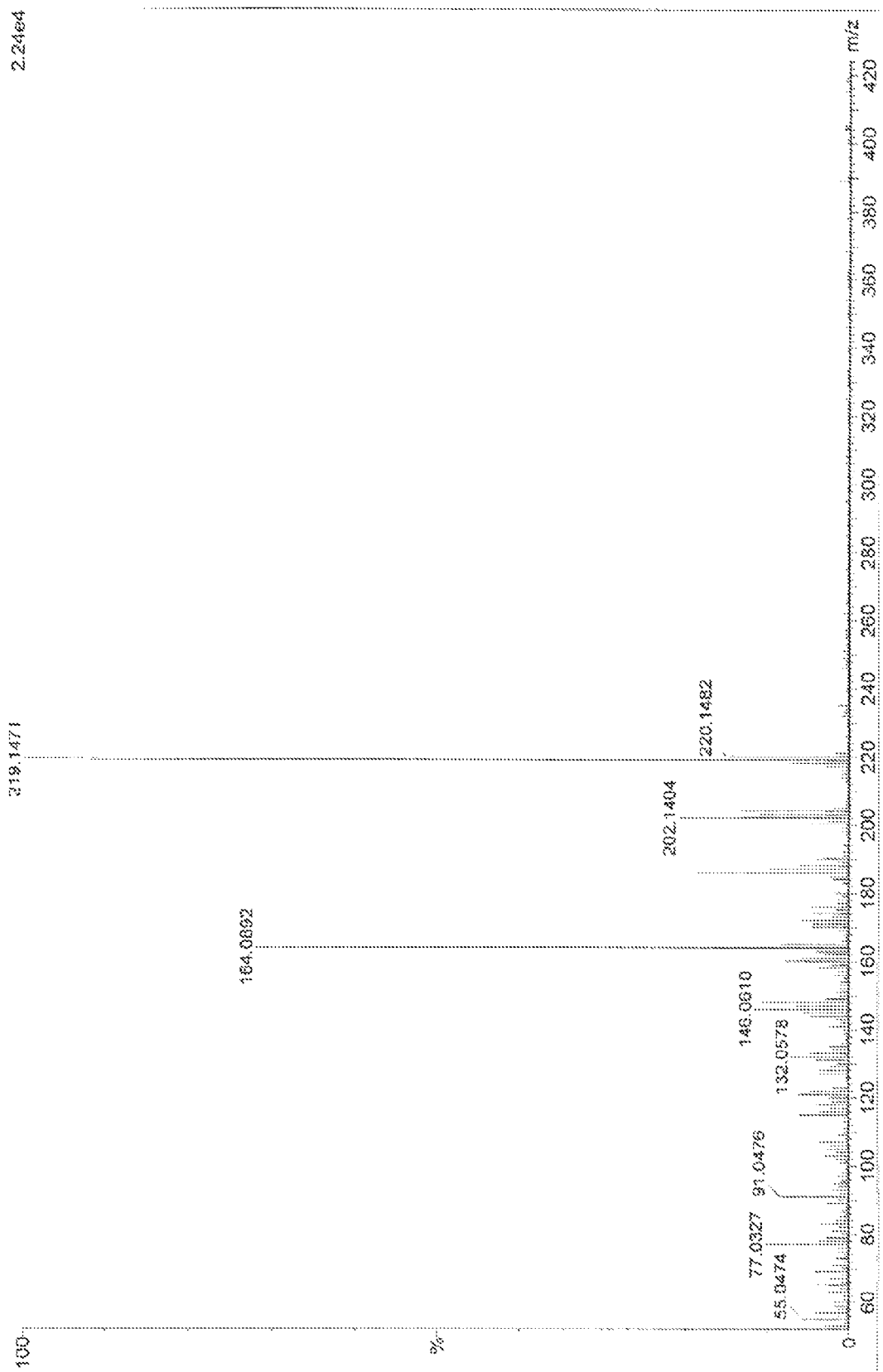
FIG. 29 shows a mass spectrum of 4-hydroxy-3-(isopenten-2-yl)-acetophenoxime.

IR spectrum in FIG. 28 shows low intensity bands between 1750-2000 cm$^{-1}$ and 1350-1550 cm$^{-1}$ assignable to the presence of benzene ring, a broad band between 3000-3500 cm$^{-1}$ associated with the presence of vibrations from a —C=N—OH and a OH group. The presence of a band at 1602 cm$^{-1}$ and the absence of a band at 1645 cm$^{-1}$ confirm the modification of the carbonyl group during the reaction.

Figure 24:
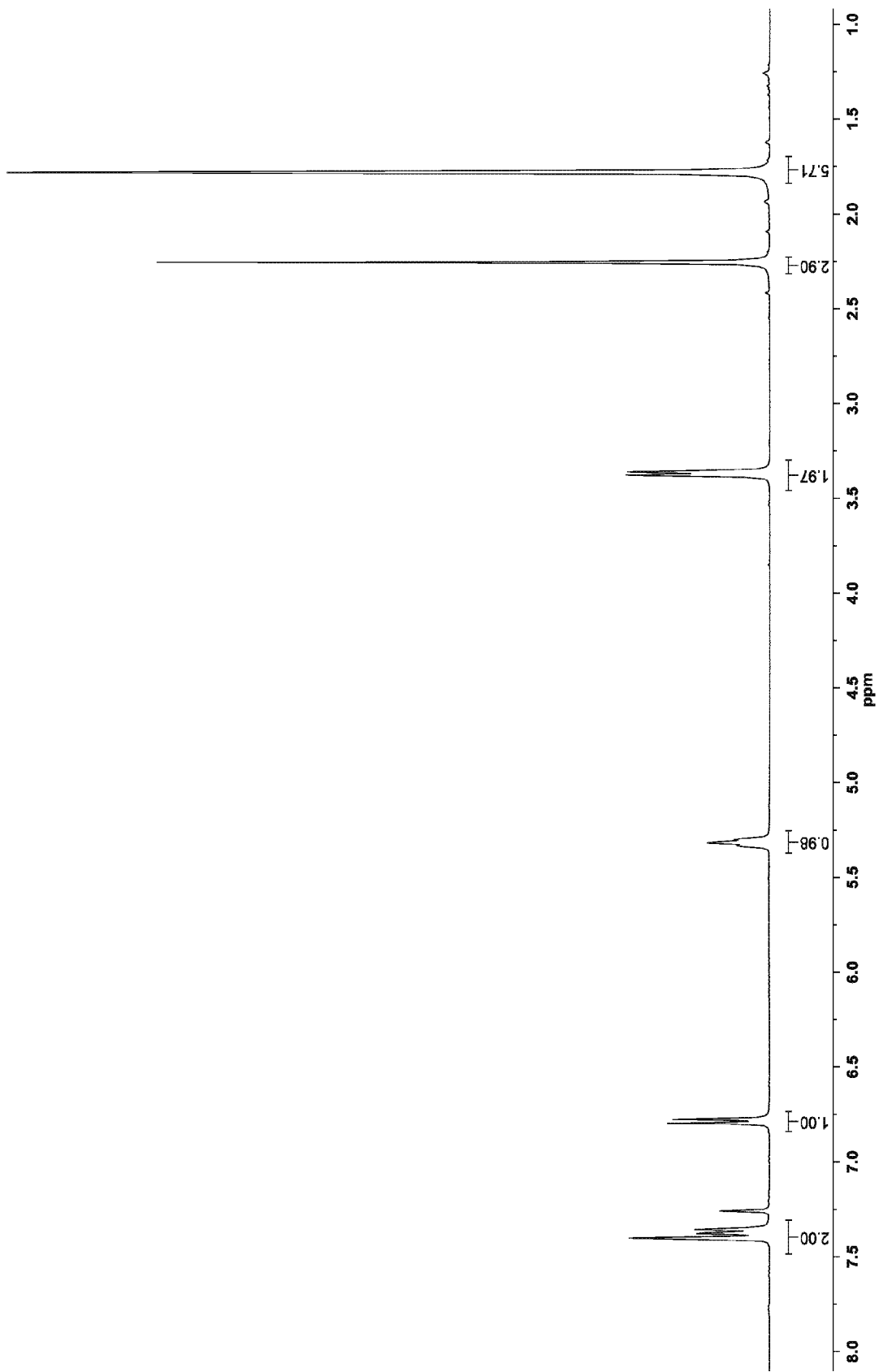
FIG. 24 shows a $^1$H-NMR spectrum de of 4-hydroxy-3-(isopenten-2-yl)-acetophenoxime.
Figure 25:
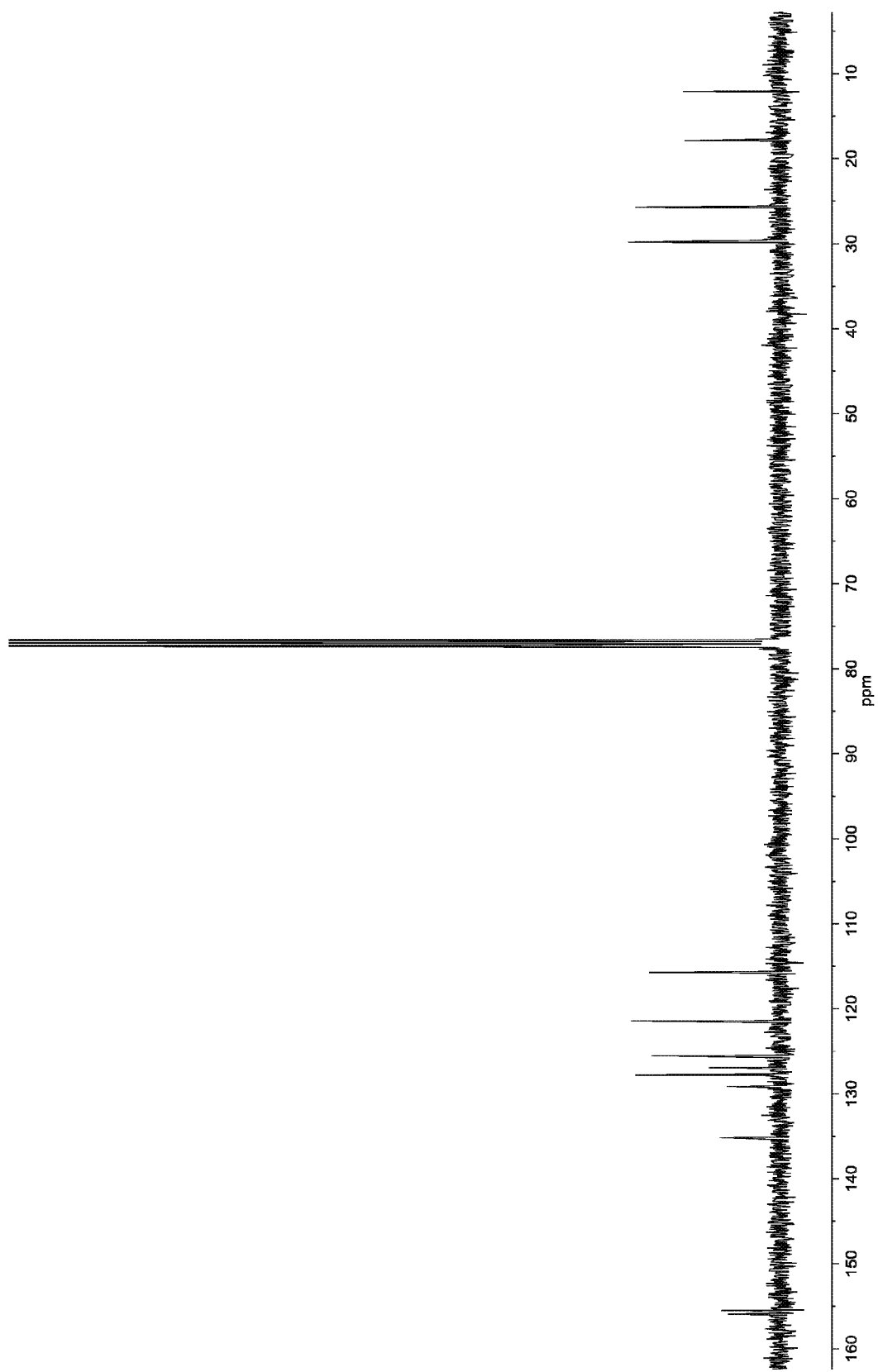
FIG. 25 shows a $^{13}$C-NMR spectrum of 4-hydroxy-3-(isopenten-2-yl)-acetophenoxime.

$^1$H-NMR y $^{13}$C-NMR spectra of FIGS. 24 and 25 show signals assignable to 15 hydrogen atoms and 13 carbon atoms, respectively. Chemical shifts and DEPT spectrum indicated the presence of three $CH_3$, an $\alpha$ $CH_2$ to the aromatic ring, three aromatic CH groups, an olefinic CH group, and 5 $sp^2$-type quaternary carbons. A methyl group is inherent to ketoxime group ($CH_3$—C=N). This methyl is shifted upfield at δ 2.26 ppm, relative to the methyl corresponding to the Metabolite (A) precursor showing at δ 2.60 ppm. The remaining two methyl groups are vinyl methyl, see Table 4.

TABLE 4

Data from $^1$H-NMR and $^{13}$C-NMR for Oxime (1) from the metabolite (A)

| Position | $δ_H$ (mult), (J Hz) | $δ_C$ |
|---|---|---|
| 1 | — | 115.47 |
| 2 | 7.40 | 127.790 |
| 3 | — | 126.93 |
| 4 | — | 129.14 |
| 5 | 6.79 (d). (8.3) | 115.72 |
| 6 | 7.37 | 125.52 |
| 7 | 3.37 (d). (7.1) | 29.87 |
| 8 | 5.31 (t). (6.2) | 121.45 |
| 9 | — | 135.15 |
| 10 | 1.78 (s) | 25.77 |
| 11 | — | 17.90 |
| 12 | — | 155.91 |
| 13 | 2.26 (s) | 12.12 |
| OH | — | — |

All $^1$H-NMR and $^{13}$C-NMR spectra were recorded in CDCl$_3$ using TMS at 400 and 100 MHz, respectively A signal in $^{13}$C-NMR spectrum that resonates at δ 155.91 ppm is observed, which corresponds to a carbon double bonded to nitrogen (C=N), signal characteristic of oximes (C=N), this new signal replaces the signal that resonated at δ 198 ppm (C-12) and corresponding to the carbonyl group of the Metabolite (A). All the above information confirms the formation of the reaction product.

Figure 27:
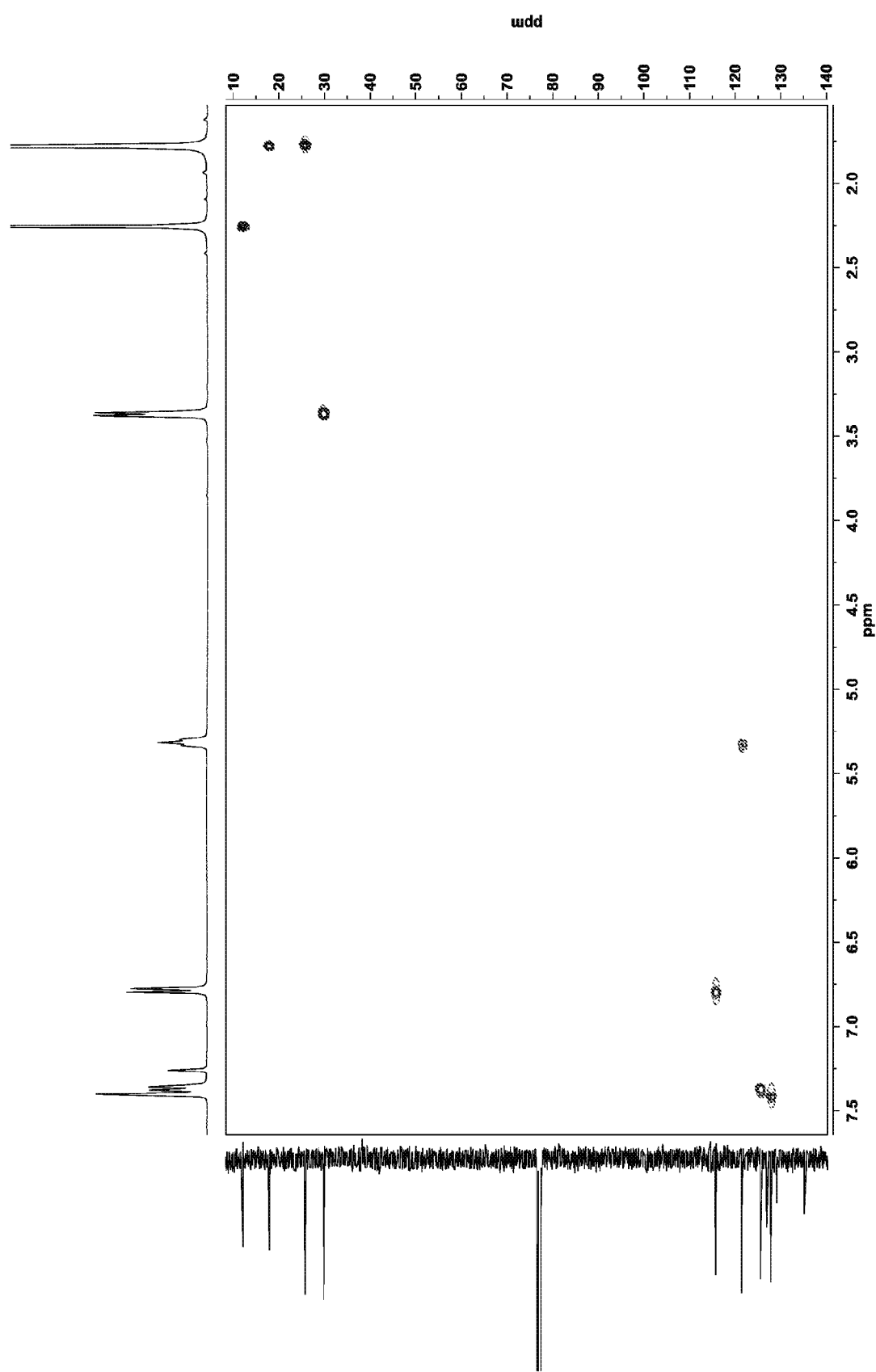
FIG. 27 shows a HSQC spectrum of 4-hydroxy-3-(isopenten-2-yl)-acetophenoxime.

HMQC spectrum in FIG. 27 shows the oxime derived.

Coupling patterns deduced by HMBC spectrum are indicated in Table 5.

Figure 26:
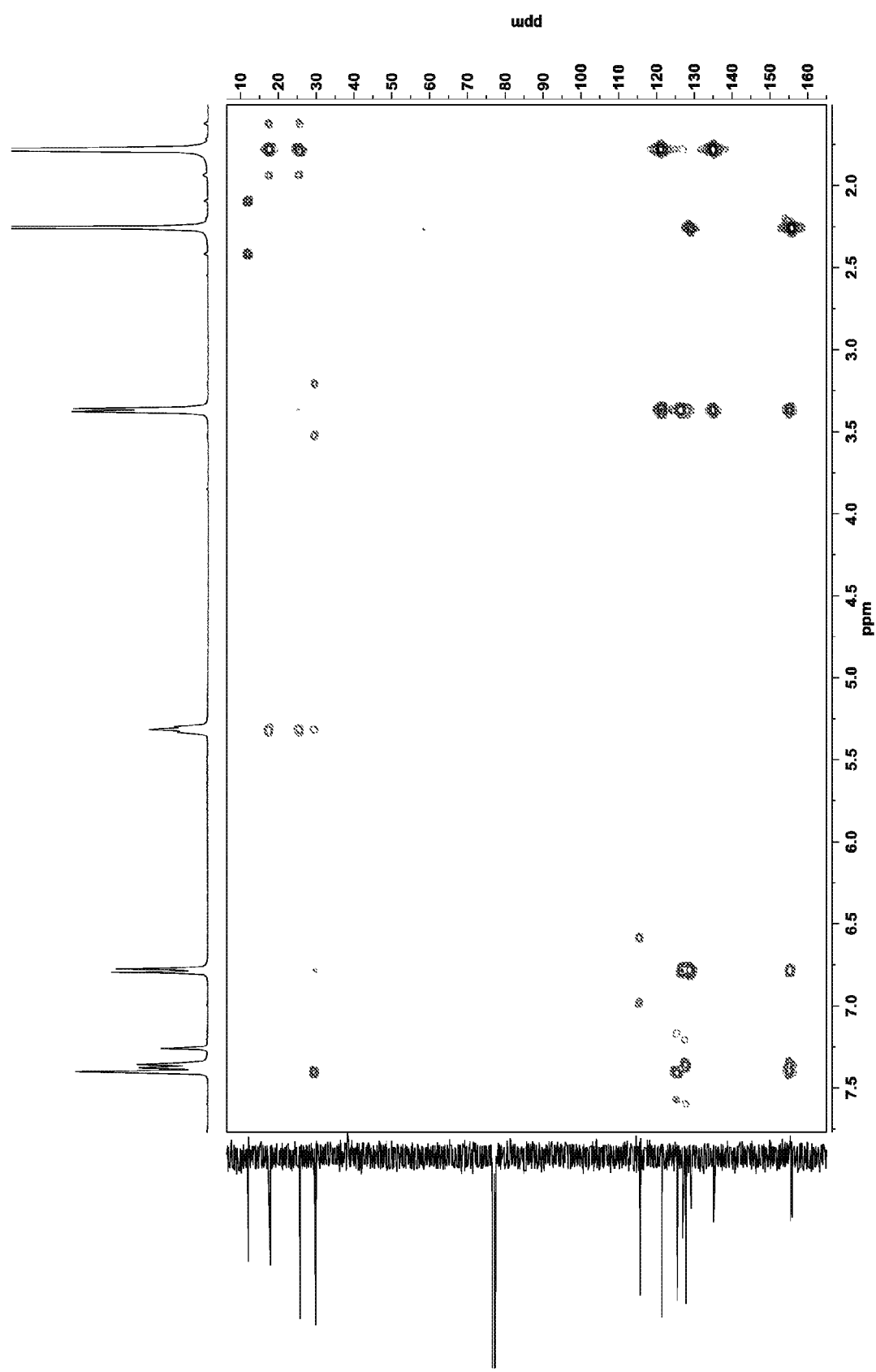
FIG. 26 shows a HMBC spectrum of 4-hydroxy-3-(isopenten-2-yl)-acetophenoxime.

Molecular structure of 4-hydroxy-3-(isopenten-2-yl)-acetophenoxime and connectivity scheme of FIG. 26 deduced by HMBC are shown below.

TABLE 5

Connectivity for 4-hydroxy-3-(isopenten-2-yl)-acetophenoxime deduced by HMBC

| Position | $δ_H$ (ppm) | Coupling Patterns |
|---|---|---|
| 2 | 7.40 | C1, C3 and C12 |
| 5 | 6.79 | C1, C3, C4 and C6 |
| 6 | 7.37 | C1 and C12 |
| 7 | 3.37 | C2, C3, C4, C8 and C9 |
| 8 | 5.31 | C7, C10 and C11 |
| 10 | 1.78 | C8 and C9 |
| 11 | 1.78 | C8 and C9 |

Oxime of Metabolite (B) (6-hydroxy-2-isopropenyl-5-acetyloxime-2,3-dihydrobenzofuran)

6-hydroxy-2-isopropenyl-5-acetyloxime-2,3-dihydrobenzofuran crystallized in dichloromethane as a green-gray crystal with a melting point of 76-78° C. and a molecular weight of 233, which is assignable to $C_{13}H_{15}NO_3$.

Figure 35:
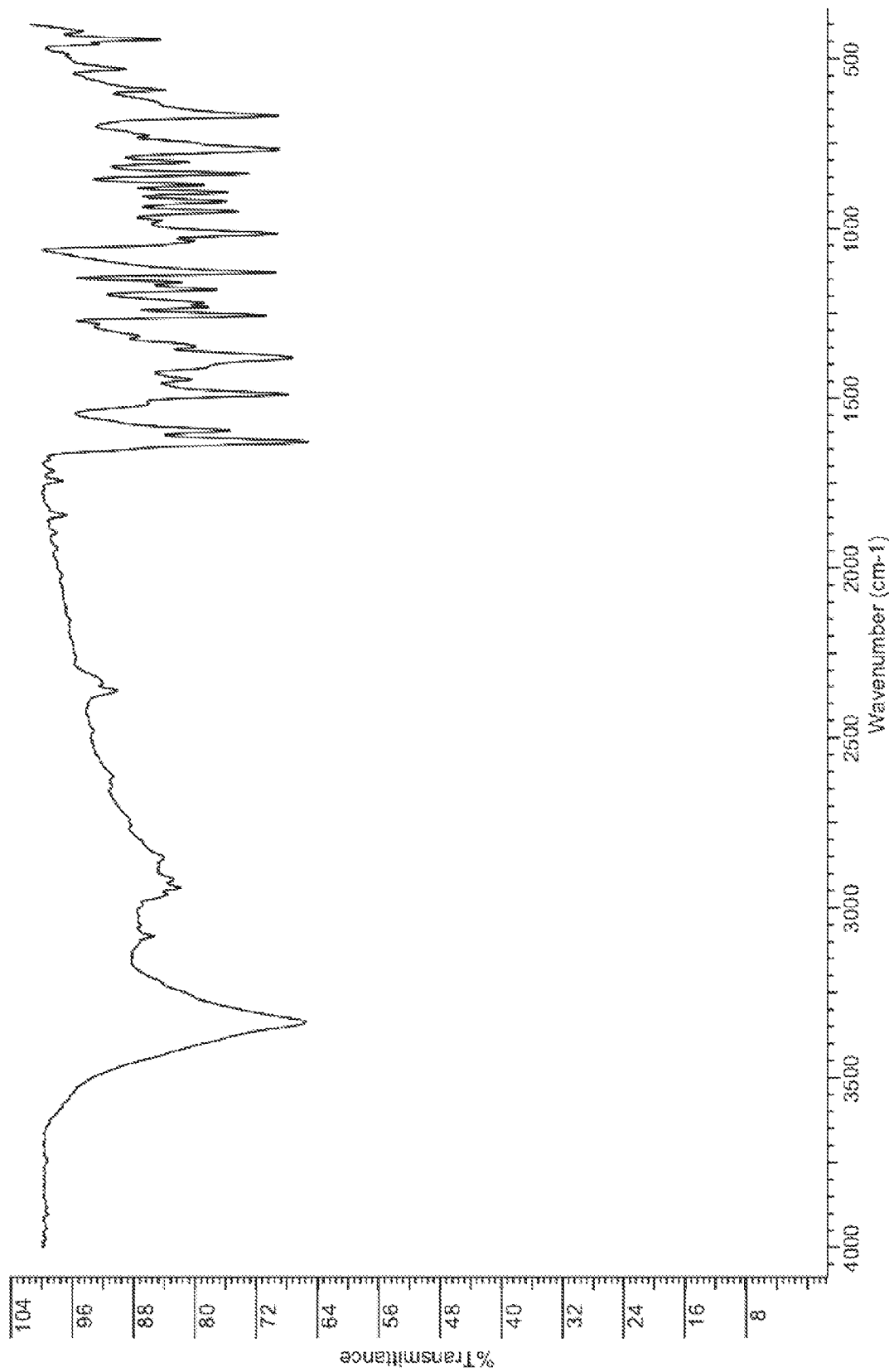
FIG. 35 shows a IR spectrum of 6-hydroxy-2-isopropenyl-5-acetyloxime-2,3-dihydrobenzofuran.
Figure 36:
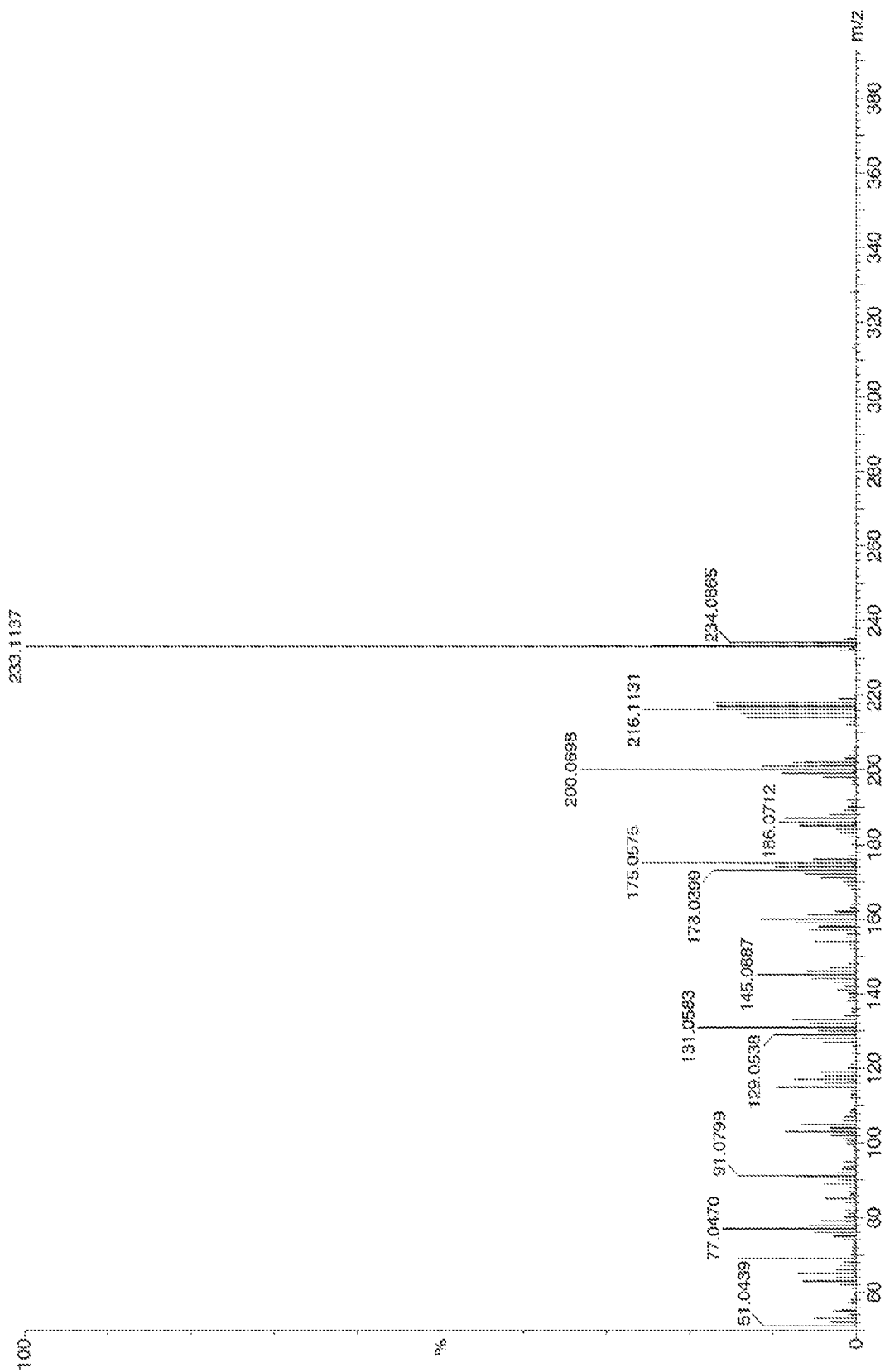
FIG. 36 shows a mass spectrum of 6-hydroxy-2-isopropenyl-5-acetyloxime-2,3-dihydrobenzofuran.

IR spectrum of FIG. 35 shows low intensity bands between 1800-2000 cm$^{-1}$ and 1400-1500 cm$^{-1}$ assignable to the presence of benzene ring, a broad band between 3000-3500 cm$^{-1}$ associated with the presence of vibrations of a —C=N—OH and OH group. The presence of a band at 1625 cm$^{-1}$ and the absence of an band at 1640 cm$^{-1}$ confirm the modification of the carbonyl reaction during the reaction.

Figure 30:
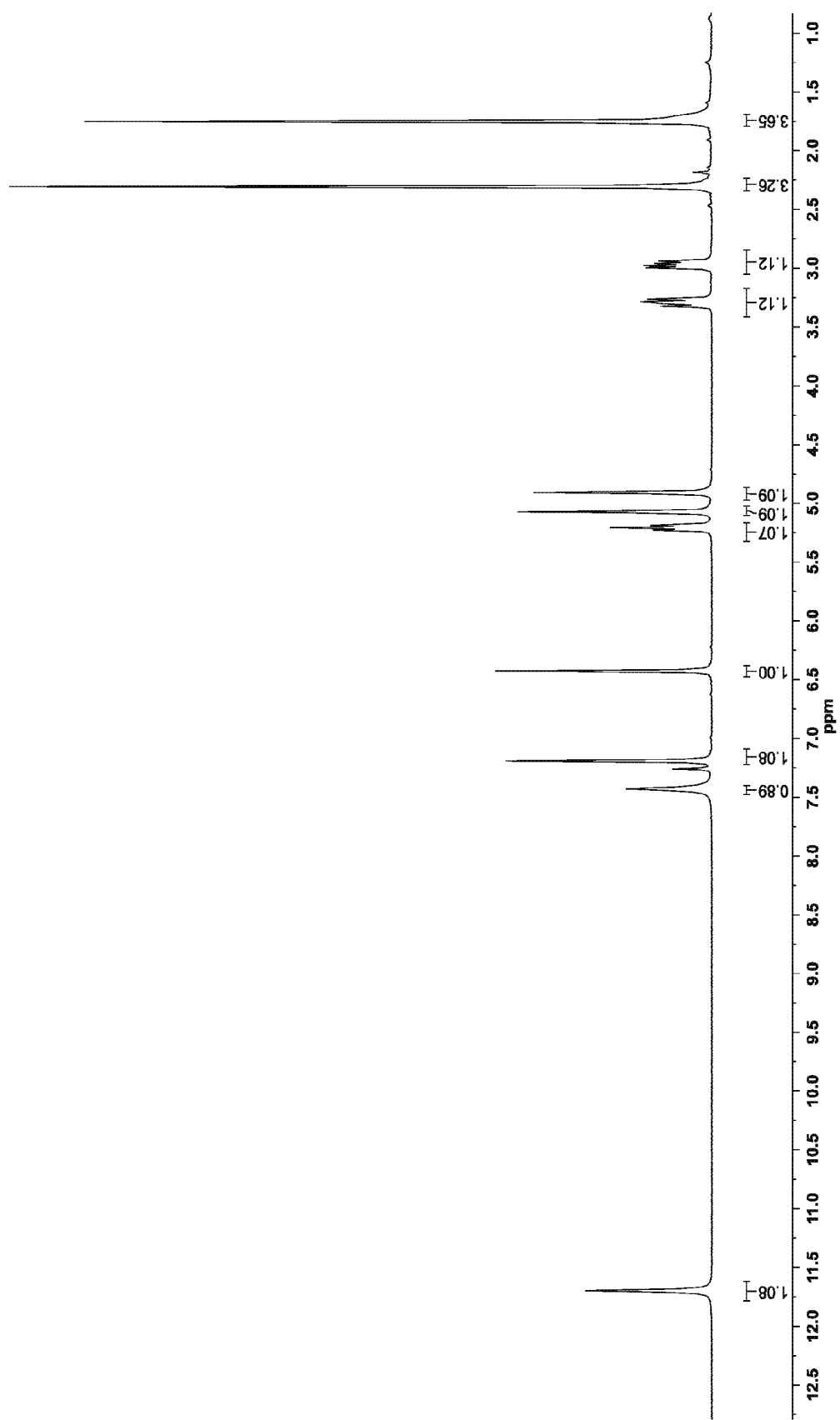
FIG. 30 shows a $^1$H-NMR spectrum of 6-hydroxy-2-isopropenyl-5-acetyloxime-2,3-dihydrobenzofuran.
Figure 31:
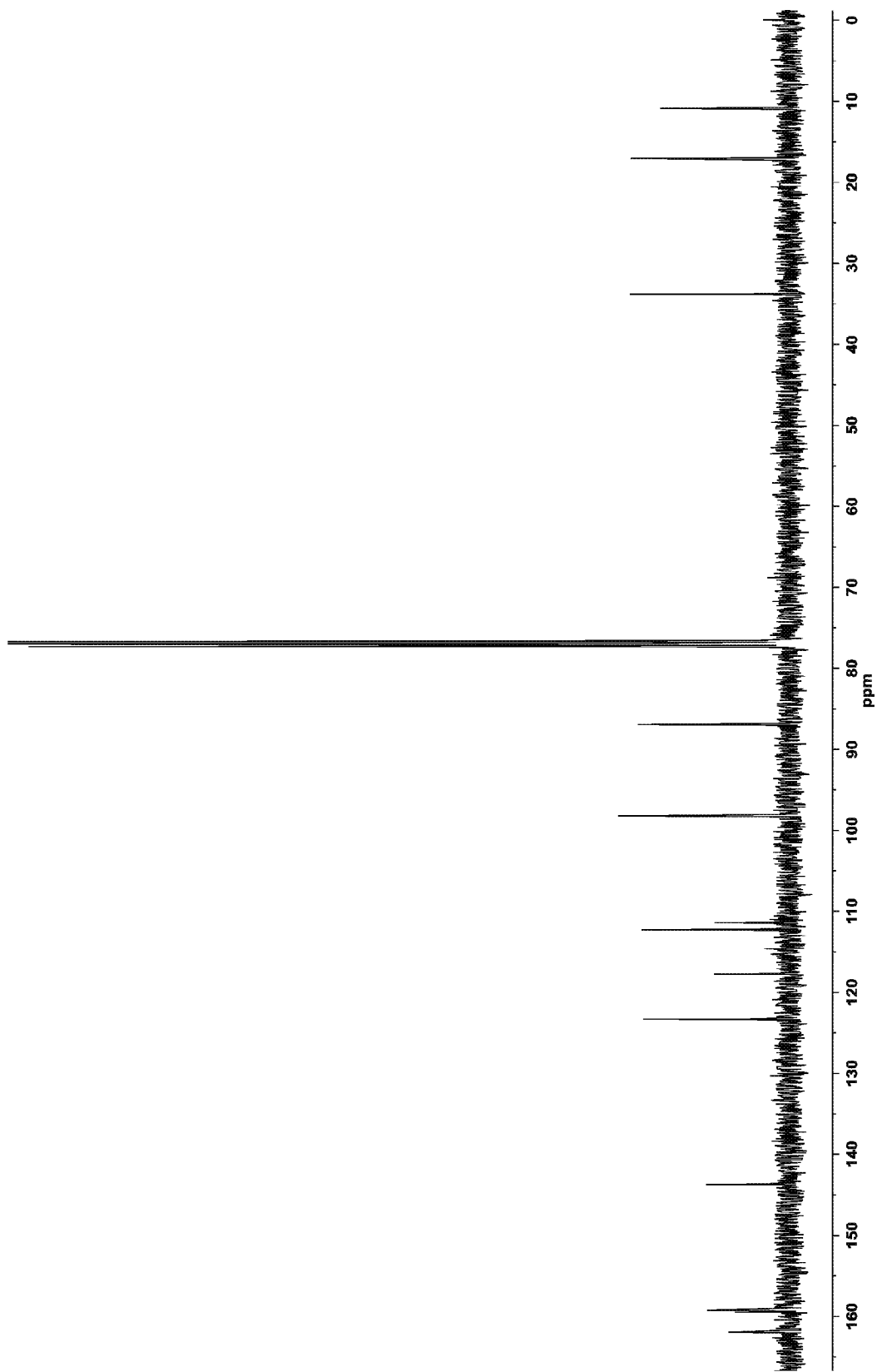
FIG. 31 shows a $^{13}$C-NMR spectrum of 6-hydroxy-2-isopropenyl-5-acetyloxime-2,3-dihydrobenzofuran.
Figure 32:
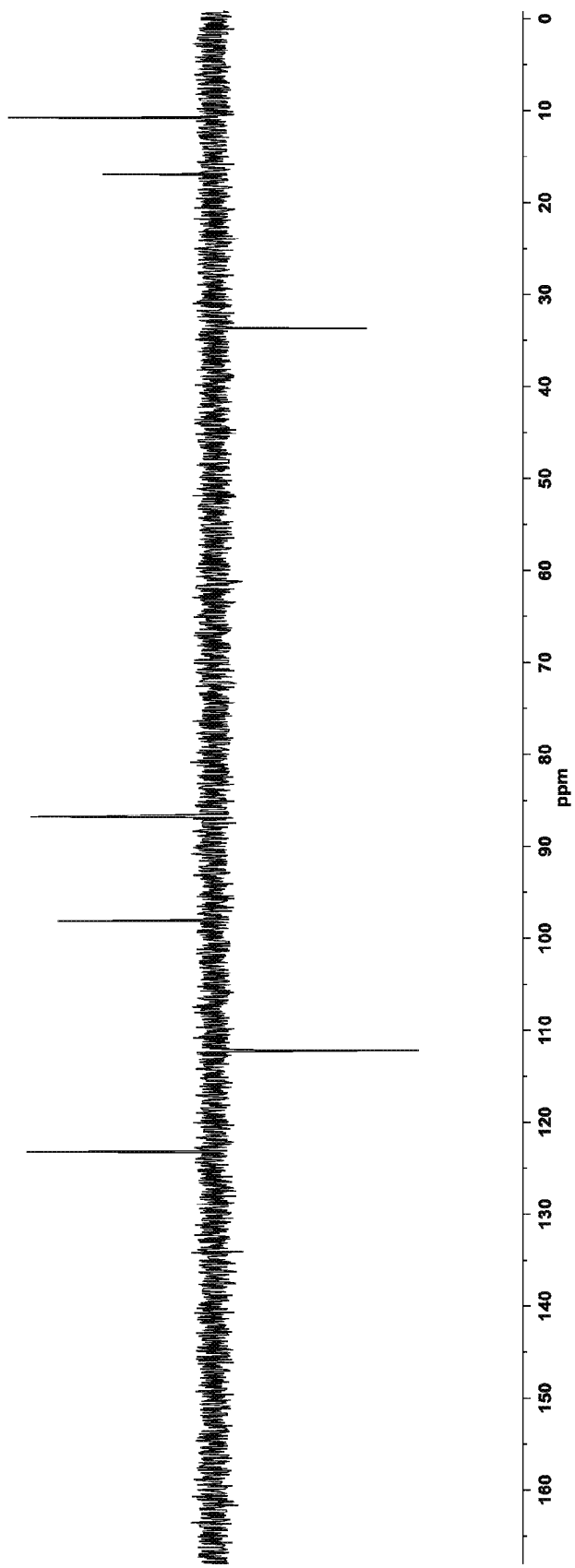
FIG. 32 shows a DEPT spectrum of 6-hydroxy-2-isopropenyl-5-acetyloxime-2,3-dihydrobenzofuran in CDCl$_3$.

$^1$H-NMR y $^{13}$C-NMR spectrum of FIGS. 30 y 31, show signals assignable to 14 hydrogen atoms and to 13 carbon atoms, respectively. Chemical shifts and DEPT spectrum of FIG. 32 clearly indicated the presence of two $CH_3$, an $\alpha CH_2$ to the aromatic ring, a $sp^2$-type $CH_2$, two aromatic CH, a $sp^3$CH and six $sp^2$-type quaternary carbons.

One of these carbons corresponds to the ketoxime function (C=N—OH) (C—12), shown by the upfield shifted signal, in the $^{13}$C-NMR spectrum, this carbon resonates at δ 161.95 ppm (C-12), while the carbonyl group of the precursor (C-12) resonates at δ 202.20 ppm (Table 6).

One of the methyl groups corresponds to a ketoxime group ($CH_3$—C=N), this methyl is upfield shifted at δ 2.30 ppm and at δ 10.90 ppm, relative to the methyl cetonic of the Metabolite (B) precursor that is showing at δ 2.56 ppm y δ 26.47 ppm.

TABLE 6

Data from $^1$H-NMR and $^{13}$C-NMR for Oxime (2) from the metabolite (B)

| Position | $δ_H$ (mult), (J Hz) | $δ_C$ |
|---|---|---|
| 1 | — | 159.48 |
| 2 | 7.19 (s) | 123.33 |
| 3 | — | 117.74 |
| 4 | — | 114.57 |
| 5 | 6.43 (s) | 98.23 |
| 6 | — | 159.24 |
| 7 | 2.97 (dd) 3.29 (dd) (14.8. 7.6) | 33.83 |
| 8 | 5.21 (t). (8.4) | 86.94 |
| 9 | — | 143.72 |
| 10 | 5.07 (s) 4.91 (s) | 112.28 |
| 11 | 1.75 (s) | 17.01 |
| 12 | — | 161.95 |

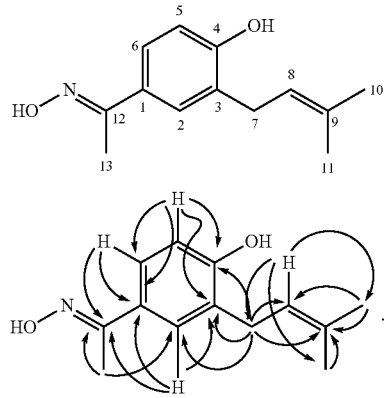

TABLE 6-continued

Data from $^1$H-NMR and $^{13}$C-NMR for
Oxime (2) from the metabolite (B)

| Position | $\delta_H$ (mult), (J Hz) | $\delta_C$ |
|---|---|---|
| 13 | 2.30 (s) | 10.90 |
| OH | 11.70 | — |

All $^1$H- and $^{13}$C- NMR spectra were recorded in CDCl$_3$ using TMS at 400 and 100 MHz, respectively Spectroscopic information allow us to establish that product formed in the reaction corresponds to 6-hydroxy-2-isopropenyl-5-acetyloxime-2,3-dihydrobenzofuran.

Coupling patterns deduced by HMBC spectrum for this oxime are shown in Table 7.

Figure 33:
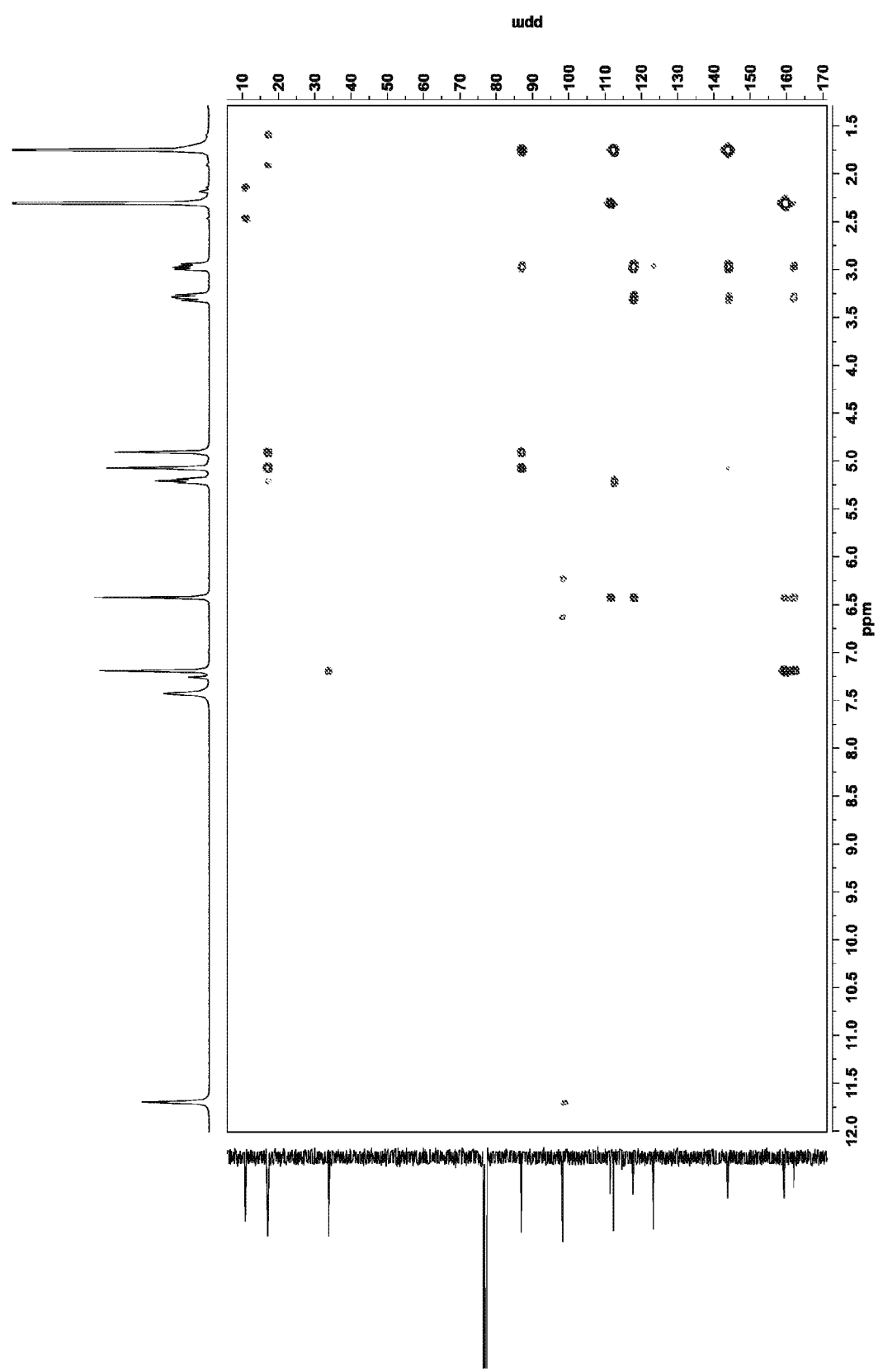
FIG. 33 shows a HMBC spectrum of 6-hydroxy-2-isopropenyl-5-acetyloxime-2,3-dihydrobenzofuran in CDCl$_3$.
Figure 34:
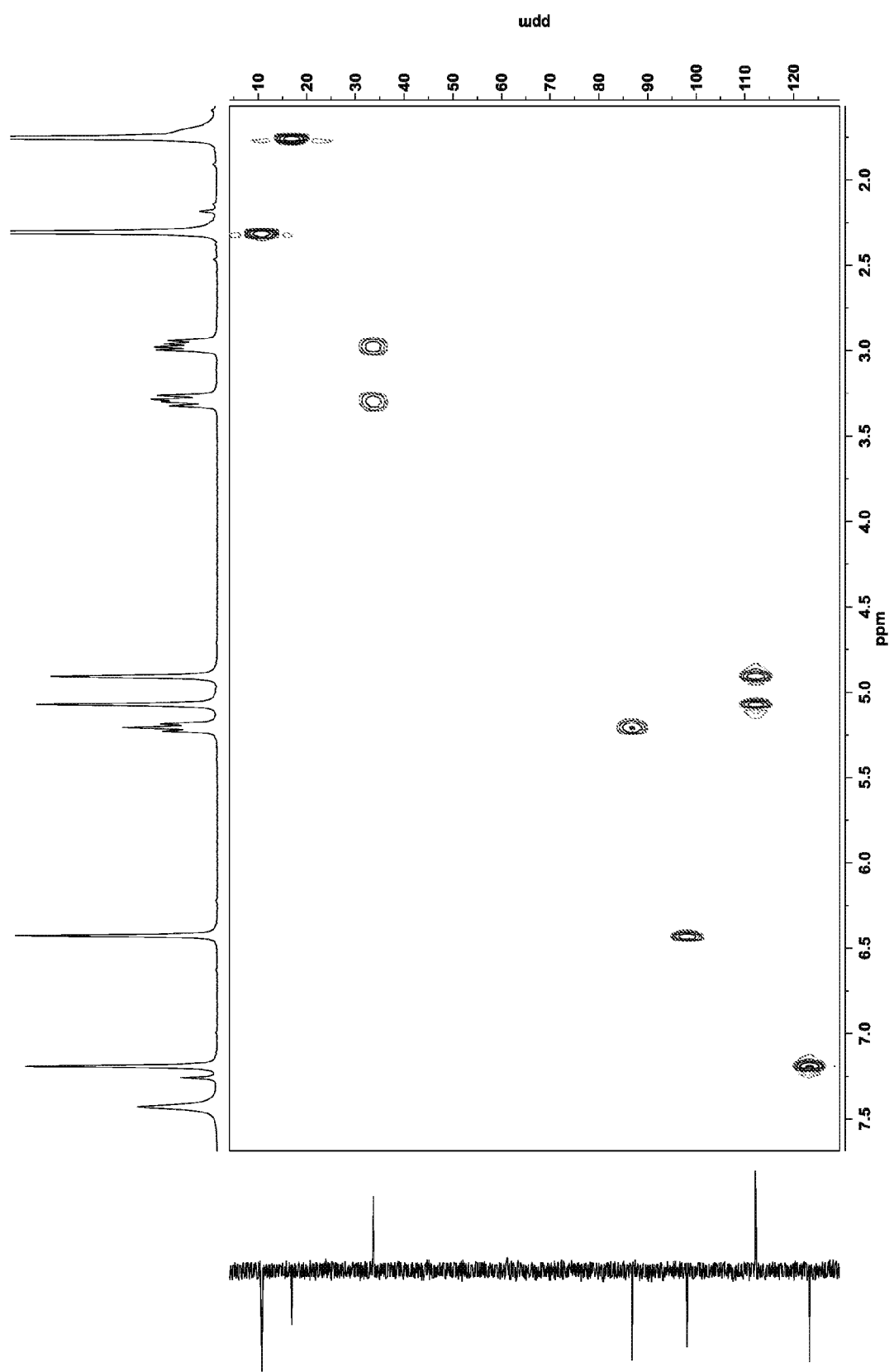
FIG. 34 shows a HMQC spectrum of 6-hydroxy-2-isopropenyl-5-acetyloxime-2,3-dihydrobenzofuran.

Molecular structure of 6-hydroxy-2-isopropenyl-5-acetyloxime-2,3-dihydrobenzofuran and connectivity scheme of FIG. 33 deduced by HMBC are shown below:

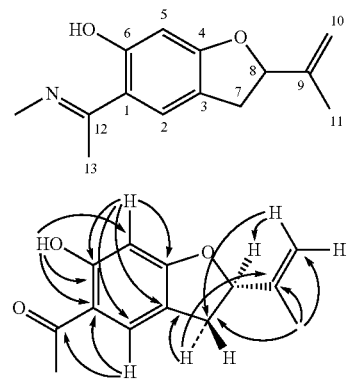

TABLE 7

Connectivity for 6-hydroxy-2-isopropenyl-5-acetyloxime-
2,3-dihydrobenzofurandeduced by HMBC

| Position | $\delta_H$ (ppm) | Coupling Patterns |
|---|---|---|
| 2 | 7.19 | C1, C3 and C12 |
| 5 | 6.43 | C1, C3, C4 and C5 |
| 7 | 2.97 3.29 | C3, C8 and C9 |
| 8 | 5.21 | C10 |
| 10 | 5.07 4.91 | C8 and C11 |
| 11 | 1.75 | C8, C9 and C10 |
| 13 | 2.30 | C1 |
| OH | 11.70 | C5 |

Example 3

The following describes application Examples of the hypotensive and vasodilatory activity of isolated metabolites and oximes thereof Determination of Biological Activity Animals Animals used were female albino rats of the Sprague-Dawley strain, obtained from the vivarium of the Universidad de Antofagasta. Two groups of animals were used separated by age:

Group I:

10-14 months old rats with an average weight of 400±70 g, were used for in vivo experiments. These animals were chosen according to their baseline health status of mild hypertension.

Group II:

3-5 months old rats with an average weight of 270±30 g, were used for vascular reactivity experiments.

All animals were kept under standard environmental conditions of temperature, humidity and light cycles, with access to food (Champion®, Chile) and water ad libitum.

Animals were fasted 24 hours before each experiment.

Protocols for all experiments were approved by the Ethics Committee on Scientific Research of the Universidad de Antofagasta, CEIC REV/200.

Drugs

Thiopental sodium was obtained from Bestpharma Laboratories. Phenylephrine (PHE), acetylcholine (ACh), propranolol (Prop), were obtained from Sigma-Aldrich and sodium nitroprusside (SNP) was purchased from Merck Chemicals.

In Vivo Tests—Hypotensive Effect in Anesthetized Rats In vivo experiments were performed using the following protocol. Group I rats were anesthetized with a 5% sodium thiopental aqueous solution at doses of 50 mg/kg animal body weight by intraperitoneal injection. The femoral vein was exposed and cannulated with a PE-10 polystyrene catheter for administering extracts, metabolites and drugs. The right carotid artery was exposed and cannulated using a PE-50 polystyrene catheter filled with heparinized saline (100 IU/mL). This catheter was connected to a pressure transducer (TSD104A) coupled to a data acquisition unit MP100 (BIOPAC Systems Inc) for recording blood pressure. The trachea was exposed and cannulated to facilitate spontaneous breathing of animals. Simultaneously, an ECG recording in derivation II (DII-ECG) was performed using an ECG100B (BIOPAC Systems Inc) module connected to a data acquisition unit MP100. The level of anesthesia of the animals was under constant supervision, so as to remain within surgical levels.

After animals were stabilized for 30 min post-surgery, 0.1 ml of each plant extract was administered at concentrations of 5, 10, 20 and 40 mg/kg animal body weight, followed by 0.1 mL of saline. Prior to administration of the next dose, blood pressure and ECG recording were monitored until complete recovery of baseline parameters (pressure and ECG). Effects of each administered dose was measured relative to changes in mean blood pressure, diastolic blood pressure, systolic blood pressure, electrocardiographic changes and compared against the effect of propranolol as a positive control at concentration of 10 mg/Kg$_{weight}$. After completion of each experiment animals were euthanized by an overdose of anesthetic, by femoral route. The results are expressed as % reduction in BMP, parameter determined using the following equation.

$$\% \ BMP \ \text{reduction} = \frac{B-E}{B} \times 100$$

Wherein B is the baseline BMP and E is the value of BMP produced by different doses studied.

All records were performed using 3.9.6.1 Acknowledge software (BIOPAC Systems Inc) and statistical analysis was performed using GraphPad Prism 5.03 software (GraphPad Software Inc.)

In Vitro Tests—Vasodilator Effect

Measure of Dilation Activity in Rat Aortic Rings

The following describes the procedure used to determine the dilation response of rat aortic rings.

Obtaining Aorta rings: Group II rats fasted 24 hours were euthanized by cervical fracture. Thoracic aorta was excised carefully from distal to proximal, from the abdominal aortic bifurcation to aortic arch and placed in a Petri dish containing Krebs-Ringer solution at room temperature with the following composition: 120 mM NaCl; 4.2 mM KCl; 1.18 mM $KH_2PO_4$; 1.2 mM $MgSO_4$; 1.3 mM $CaCl_2$; 5 mM $C_6H_{12}O_6$; and 25 mM $NaHCO_3$ pH 7.4 and constantly gasified with a mixture of 95% $O_2$ and 5% $CO_2$. After removing blood, fat and connective tissue, the aorta was transversely cut in cylindrical rings 2-3 mm in diameter.

Mounting of Rings: Each ring was mounted between two triangular stainless steel hooks, one hook was suspended in a glass rod (anchorage) and placed in a Single Organ Chamber with 10 ml Krebs-Ringer constantly aerated with 95% $O_2$ and 5% $CO_2$ gaseous mixture and maintained at 37° C. by thermo regulated pump. The second hook was connected by a thread to an Isometric Force Transducer XDCR (Radnoti Glass Technology Inc. USA.), connected to a data acquisition unit PowerLab 8/30 (ADInstruments). The data were processed using LabChart 7 Pro software, provided by ADInstruments.

Conditioning of Tissue: After being mounted rings were left to rest with no tension for 30 minutes. Subsequently Krebs-Ringer solution was replaced and rings were allowed to rest for 10 minutes. The rings were then carefully tensioned twice at intervals of 10 minutes each at 1.00 g tension value using micromanipulators. Two settings of tension at 1.40 g at 10 minutes interval each were then made. After the period of stabilization of the tissue, tissue viability was assessed by the addition of solution of 60 mM potassium chloride (KCl). After 10 minutes of contraction of the tissue, it was washed twice at intervals of 5 minutes each before the next addition of KCl. When two successive contraction controls showed similar amplitudes, the preparation was considered balanced and ready for determination of vasodilator activity of the substances.

Figure 1:
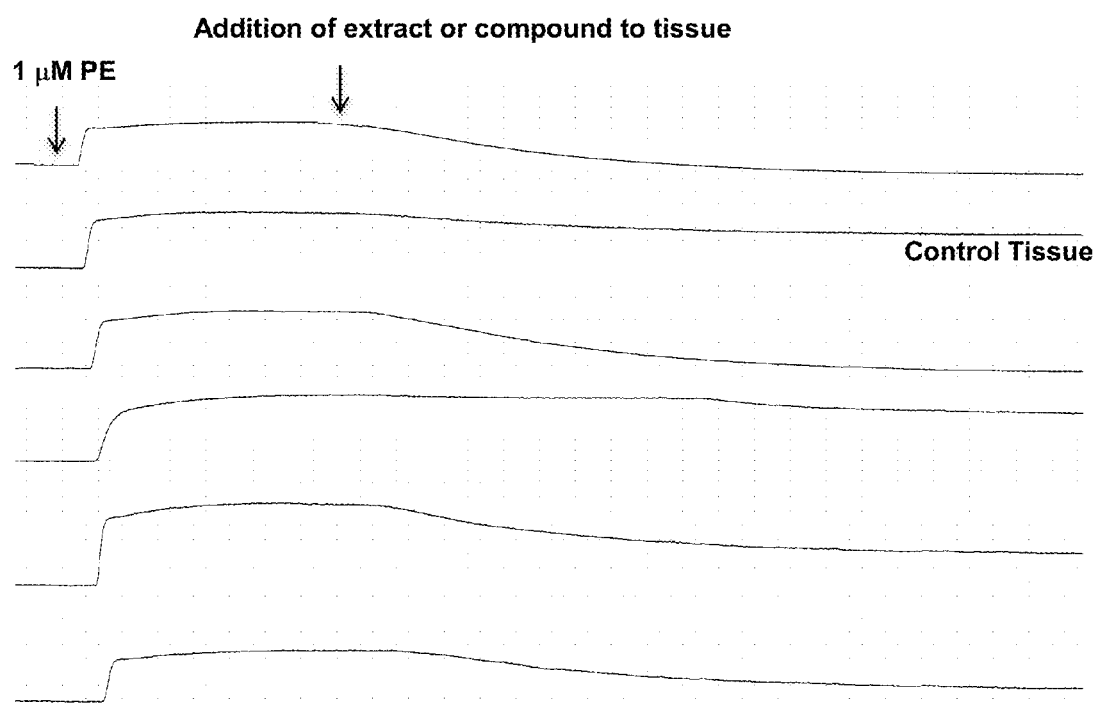
FIG. 1 shows the representative plot of phenylephrine (PHE)-induced contraction, and vasodilator effect produced by extracts or added products.

Measure of vasodilatory activity: The aortic tissue with endothelium already conditioned was applied a tension of 1.4 g, 1 μM PHE solution was added after 10 minutes. PHE was added cumulatively to each single organ bath after stabilization of PHE-induced contractile response. Stock solutions of $10^{-1}$ M concentration in DMSO were prepared to determine the vasodilatory activity of the isolated metabolites. Subsequent dilutions were made in the concentration range $10^{-10}$-$10^{-4}$ M in distilled water, so that the final concentration in the organ bath did not exceed 0.1% DMSO. The vasodilator effect was recorded for a period of 30 minutes for each of the concentrations used (FIG. 1). The results are expressed as relaxation percent using the following formula:

$$\% \text{ relaxation} = \frac{R_1 - R_2}{R_1} \times 100$$

wherein $R_1$ is the response induced by PHE and $R_2$ is the response after the extracts are added.

Statistical analysis was carried out using GraphPad Prism 5.03. software (GraphPad Software Inc.)

Figure 2:
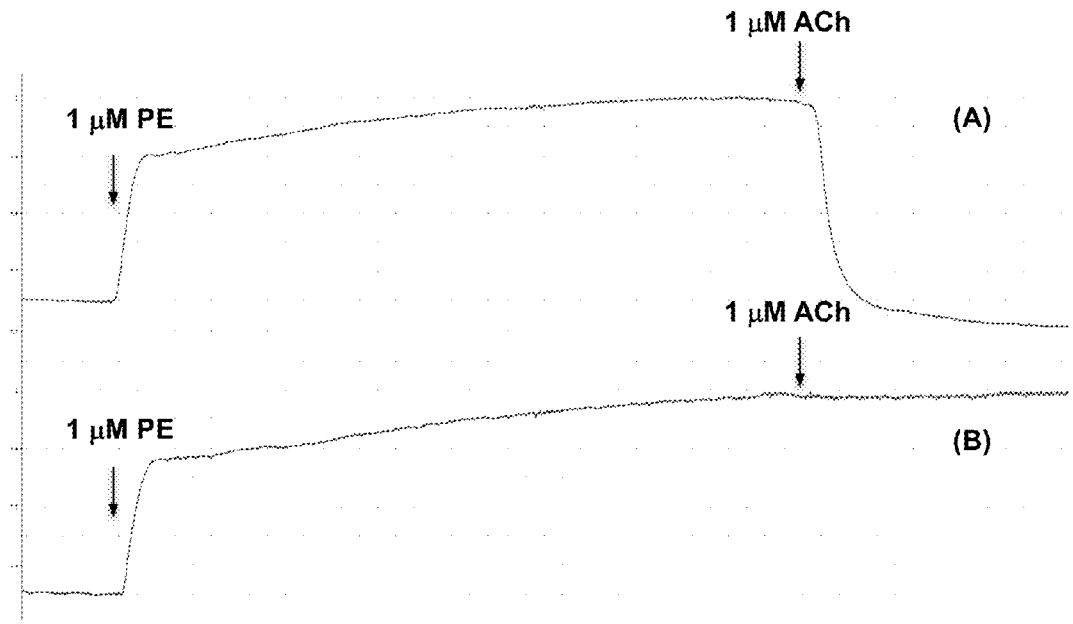
FIG. 2 shows the pharmacological verification of presence of endothelium in aorta rings. In (A) phenylephrine-precontracted rings and relaxant effect induced by addition of acetylcholine (ACh). In (B) zero ACh effect due to the absence of endothelium is observed.

Endothelium integrity was tested by addition of 1 μM ACh to rings precontracted with 1 uM PHE, and rings were considered with intact endothelium when the ACh dilator response was greater than 80%. While rings with response lower than 10% were discarded (FIG. 2).

Figure 3:
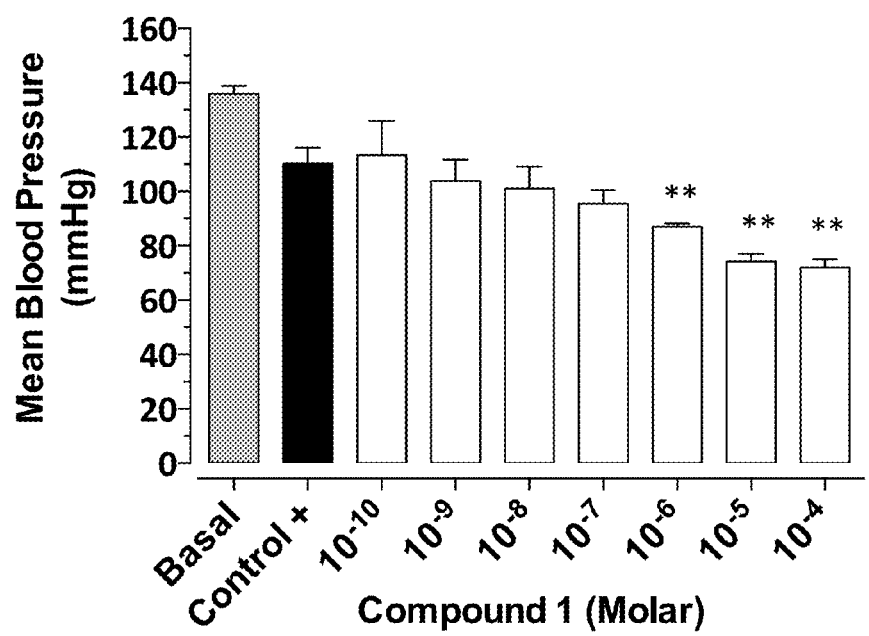
FIG. 3 shows the hypotensive effect of different concentrations of metabolite (A). Results are expressed as mean±standard error with five replications, significant differences are expressed as p. (mean±SE. n=5, **p<0.001).

Hypotensive Effect of
4-hydroxy-3-(isopenten-2-yl)acetophenone 4-hydroxy-3-(isopenten-2-yl)-acetophenone showed a significant dose-dependent hypotensive effect (Table 8). It was observed that the effect on MBP stars being significant from concentrations of $10^{-6}$ M. The maximum antihypertensive effect was achieved at doses of $10^{-4}$ M with a % MBP reduction of 46.93±1.01%. The hypotensive effect was compared against the hypotensive drug propranolol at concentration of $10^{-6}$ M. (FIG. 3).

TABLE 8

Hypotensive effect of 4-hydroxy-3-(isopenten-2-yl)-acetophenone, MBP values (mmHg), and % MBP reduction obtained after intravenous administration of metabolite (A) expressed as mean ± SE.

| Compound | Dose (M) | MBP (mmHg) | % MBP reduction |
|---|---|---|---|
| Metabolite 1 | Basal | 135.9 ± 2.98 | — |
| | Control+ | 110.1 ± 6.03 | 18.99 ± 4.35 |
| | $10^{-10}$ | 113.4 ± 12.59 | 16.56 ± 9.38 |
| | $10^{-9}$ | 103.8 ± 7.98 | 23.62 ± 5.76 |
| | $10^{-8}$ | 101.0 ± 8.06 | 25.68 ± 5.24 |
| | $10^{-7}$ | 95.56 ± 5.01 | 29.68 ± 3.42 |
| | $10^{-6}$ | 87.09 ± 1.14 | 35.92 ± 2.01 |
| | $10^{-5}$ | 74.24 ± 2.76 | 45.37 ± 1.09 |
| | $10^{-4}$ | 72.12 ± 2.92 | 46.93 ± 1.01 |

Control+ = propranolol $10^{-6}$ M

Hypotensive Effect of
4-hydroxy-3-(isopenten-2-yl)-acetophenoxime

Figure 4:
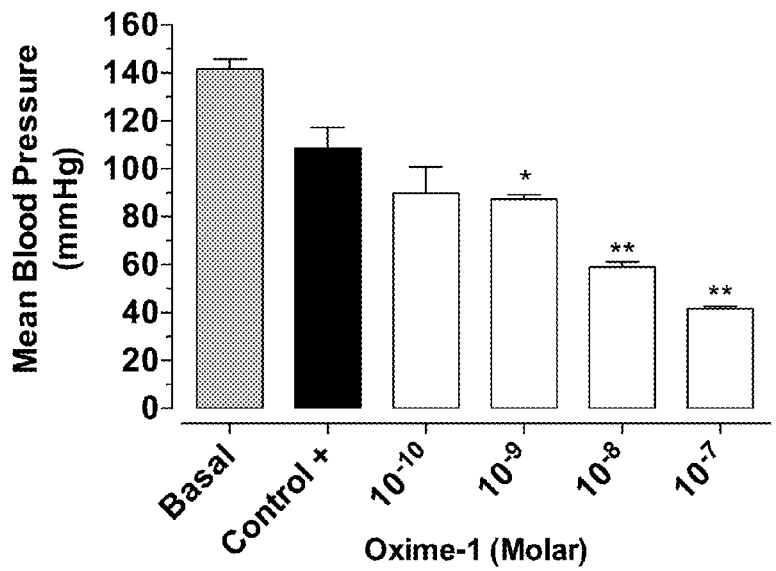
FIG. 4 shows the hypotensive effect of different concentrations of oxime (1) derived from metabolite (A). Results are expressed as mean±SE. n=5, *p<0.01**p<0.001.

Table 9 shows that oxime 4-hydroxy-3-(isopenten-2-yl)-acetophenone (oxime (1)) produced a dose-dependent hypotension. The effects on MBP started to be significant from a concentration of $10^{-9}$ M reaching its maximum effect at a dose of $10^{-7}$ M with a MBP reduction percentage of 70.61±4.32%. The effect was compared against the drug propranolol at concentration of $10^{-6}$ M as a positive control. It is important to note that doses higher than $10^{-7}$ M induced acute hypotension in animals and subsequent animal death by cardiac arrest. (FIG. 4)

TABLE 9

In vivo hypotensive effect of 4-hydroxy-3-(isopenten-2-yl)-acetophenoxime. MBP values (mmHg), and % MBP reduction obtained after intravenous administration of oxime (1), Metabolite (A) expressed as mean ± SE.

| Compound | Dose (mg/Kg$_{weight}$) | MBP (mmHg) | % MBP reduction |
|---|---|---|---|
| Oxime (1) | Basal | 141.70 ± 4.06 | — |
| | Control+ | 108.70 ± 8.55 | 22.29 ± 3.20 |
| | $10^{-10}$ | 89.84 ± 10.88 | 36.60 ± 7.90 |
| | $10^{-9}$ | 87.28 ± 1.90 | 38.41 ± 2.35 |
| | $10^{-8}$ | 59.05 ± 2.09 | 58.31 ± 3.26 |
| | $10^{-7}$ | 41.65 ± 0.85 | 70.61 ± 4.32 |

Control+ = propranolol $10^{-6}$ M

Vascular reactivity experiments were performed to establish the vasodilator action of the isolated compounds. For this, compounds at concentration of $10^{-4}$M were added to the organ chamber, the vasodilatory effect in rings with intact endothelium (E+) and without endothelium (E−) precontracted with 1 μM PHE was quantified. We performed parallel vehicle control (DMSO) to discard the relaxing effect of aortic tissue.

Figure 5:
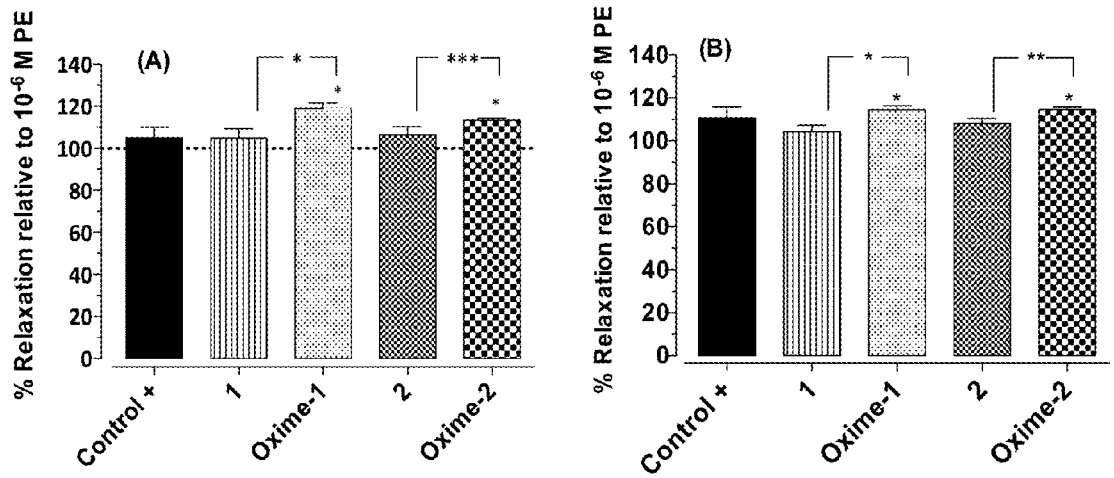
FIG. 5 (A and B) shows oximes vasodilator effect and their precursors; (A) Compounds at $10^{-4}$ M concentration versus $10^{-6}$ M Ach as a positive control in rings with intact endothelium. (B) Compounds at $10^{-4}$ M concentration versus $10^{-6}$ M NPS as a positive control in rings without endothelium. Values are expressed as mean±SE. n 5-6, *p<0.01, p<0.01 * p<0.001.

It was further noted that the compounds 4-hydroxy-3-(isopenten-2-yl)acetophenone and 6-hydroxy-2-isopropenyl-5-acetyl-2,3-dihydrobenzofuran possess vasodilator activity in most aortic rings with endothelium, reaching an $E_{max}$ of 121.6±2.09% and 135.4±3.78% respectively, which is comparable to the effect generated by $10^{-6}$ M ACh as a positive control 105.1±5.00% (FIG. 5 A).

In aortic rings without endothelium was observed that metabolites (A) and (B) reached a maximum relaxation effect of 117.9±10.69% and 145.5±4.49% respectively, these were compared with $10^{-6}$ M NPS as a positive control which reached an $E_{max}$ of 110.7±5.09% (Figure 5B).

Subsequently, derivate oximes (1) and (2) were studied at same concentrations than precursors, and it was observed that both compounds possess vasodilator effect on both aortic rings with endothelium and aortic rings without endothelium. These modified compounds reached values of $E_{max}$ of 130.2±2.54% for oxime (1) and 118.4±0.93% for oxime (2), respectively (FIG. 5A). In aortic rings without endothelium these oximes reached $E_{max}$ of 120.3±1.74% for oxime-1 y 117.7±1.00% for oxime-2 (FIG. 5 B). The vehicle used did not cause disruption of PHE contractile response (data not shown).

Based on the vasodilator response elicited by Metabolites (A) and (B), and their respective oximes (1) and (2), greater than 100%, it was decided to perform dose-response curves to establish the $EC_{50}$ parameter, which is the necessary dose to generate a 50% relaxation of tissue.

Vasodilator Effect of
4-hydroxy-3-(isopenten-2-yl)acetophenone

Figure 6:
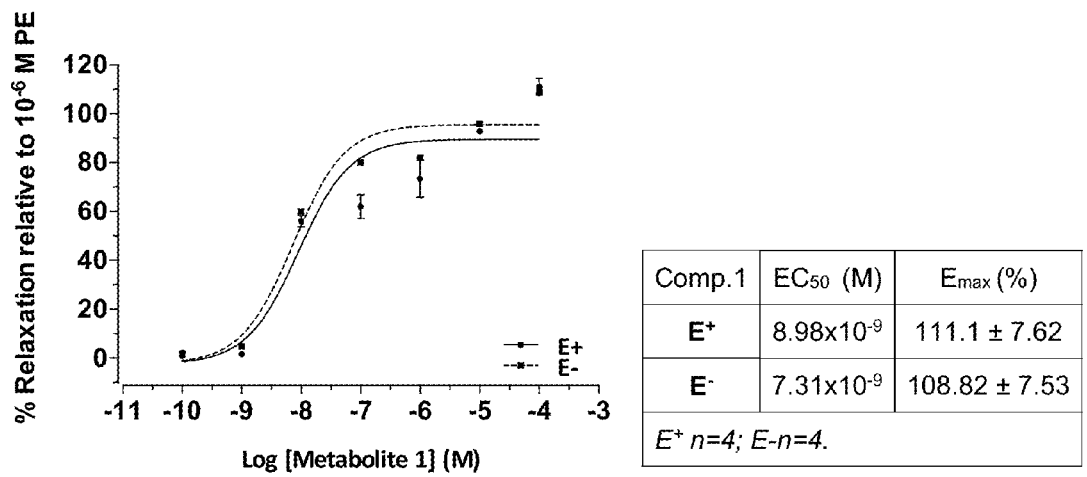
FIG. 6 shows the dose-response curve for relaxation induced by metabolite (A) in PHE-precontracted rat aorta with endothelium (E+) and without endothelium (E−) expressed as % relaxation (mean±SE).

Adding increasing doses of 4-hydroxy-3-(isopenten-2-yl)-acetophenone (metabolite (A)) in rings with intact endothelium ($E^+$) produced a dose-dependent vasodilation (FIG. 6). The vasodilator effect started from concentrations of $10^{-8}$ M and reached its maximum effect at $10^{-4}$ M, with a $E_{max}$ value of 111.1±7.62%. The concentration of 4-hydroxy-3-(isopenten-2-yl)-acetophenone required to achieve 50% relaxation of tissue ($EC_{50}$) was 8.98×$10^{-9}$ M. It is important to note that response of this compound for the tissue without endothelium ($E^-$) was similar to that observed for rings with intact endothelium, i.e., a dose-dependent relaxation occurs with an $E_{max}$ of 108.8±7.53% at a concentration of $10^{-4}$ M and an $EC_{50}$ of 7.31×$10^{-9}$ M (FIG. 6).

Vasodilator Effect of 6-hydroxy-2-isopropenyl-5-acetyl-2,3-dihydrobenzofuran

Figure 7:
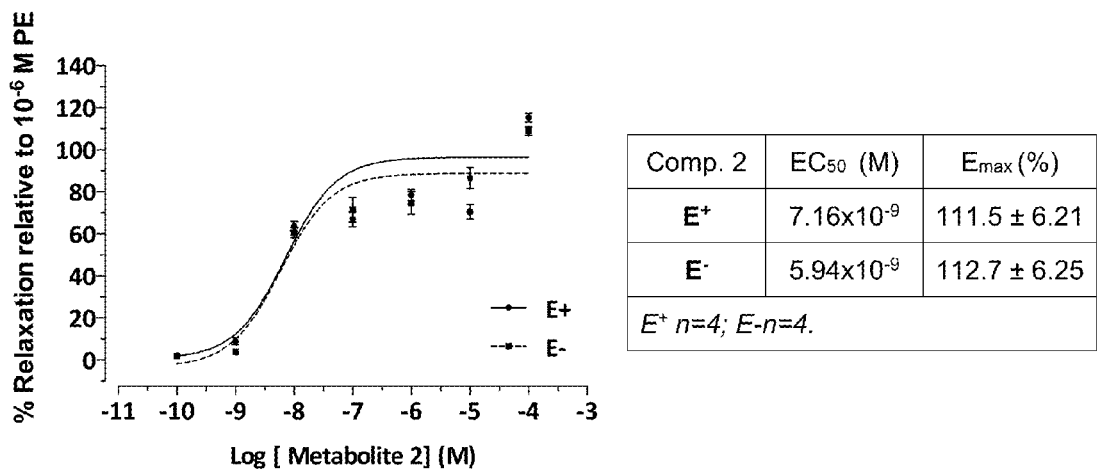
FIG. 7 shows the dose-response curve for relaxation induced by metabolite (B) in PHE-precontracted rat aorta with endothelium (E$^+$) and without endothelium (E$^-$) expressed as % relaxation (mean±SE).

Adding increasing doses of 6-hydroxy-2-isopropenyl-5-acetyl-2,3-dihydrobenzofuran (metabolite (B)) caused a dose-dependent vasodilation in aortic rings with intact endothelium (FIG. 7). The vasodilator effect started from concentrations of $10^{-8}$ M and reached its maximum effect at a concentration of $10^{-4}$ M, $E_{max}$ 111.5±6.21%. The concentration required to achieve 50% relaxation of tissue ($EC_{50}$) was 7.16×$10^{-9}$ M. In tissue without endothelium ($E^-$) vasodilatory response of this compound was similar to that observed for the rings with endothelium, i.e., a dose-dependent relaxation occurs with an $E_{max}$ of 108.8±7.53% at concentration of $10^{-4}$ M and an $EC_{50}$ of 5.94×$10^{-9}$ M (FIG. 7).

Vasodilator Effect of
4-hydroxy-3-(isopenten-2-yl)-acetophenoxime

Figure 8:
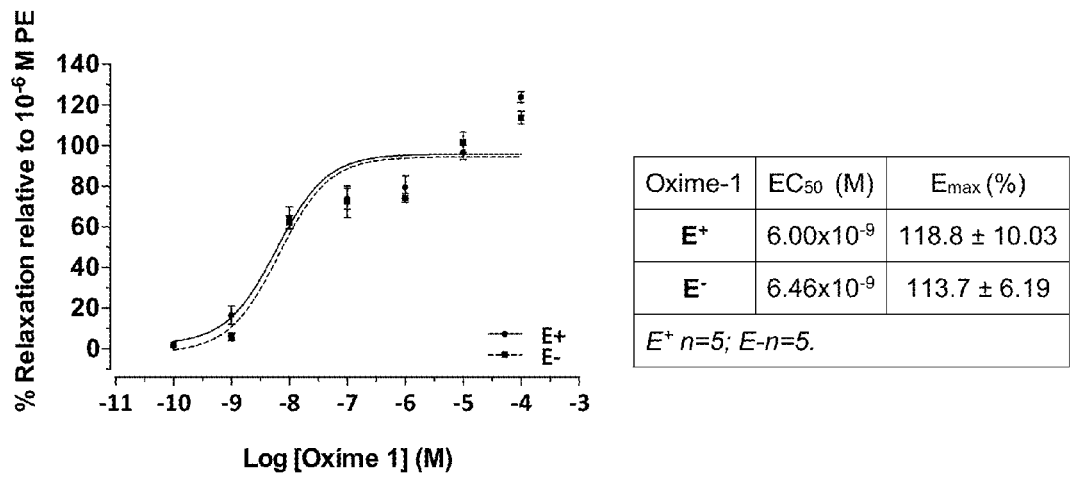
FIG. 8 shows dose-response curves for relaxation induced by metabolite (A) oxime, oxime (1), in PHE-precontracted rat aorta with endothelium (E$^+$) and without endothelium (E$^-$), expressed as % relaxation (mean±SE).

Adding increasing doses of the oxime (1) of 4-hydroxy-3-(isopenten-2-yl)acetophenone to organ baths containing aorta arteries with intact endothelium (E+) caused dose-dependent vasodilation as shown in FIG. 8. For this compound the vasodilator effect was first observed from concentrations of $10^{-9}$ M and reached a maximal effect at concentration of $10^{-4}$ M. With a value of 118.8±3.92% and an $EC_{50}$ value of 6.00×$10^{-9}$ M. It is important to note that from concentrations of $10^{-5}$ M, the compound induced 100% of tissue relaxation (101.6±0.90%). Oxime-1 also produced a dose-dependent vasodilation in rings without endothelium (E−), reaching an $E_{max}$ of 113.7±6.19% and an $EC_{50}$ value of 6.56×$10^{-9}$ M.

Figure 9:
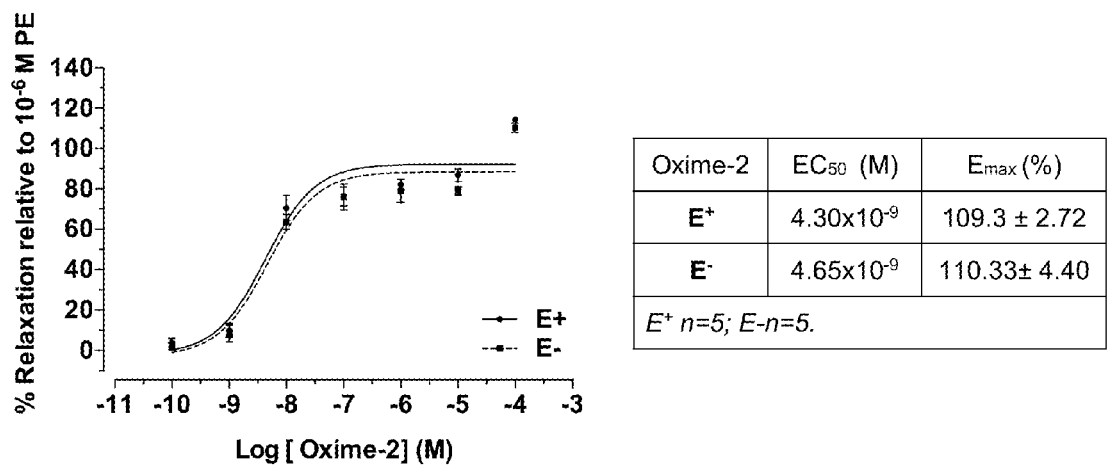
FIG. 9 shows dose-response curves for relaxation induced metabolite (B) oxime, oxime (2), in PHE-precontracted rat aorta with endothelium (E$^+$) and without endothelium (E$^-$), expressed as % (mean±SE).

Vasodilator Effect of 6-hydroxy-2-isopropenyl-5-acetyloxime-2,3-dihydrobenzofuran Adding increasing doses of the oxime (2) of 6-hydroxy-2-isopropenyl-5-acetyl-2,3-dihydrobenzofuran in organ baths containing aorta arteries with intact endothelium (E+) caused dose-dependent vasodilatation as shown in FIG. 9. For this compound the vasodilator effect was first observed at concentrations of $10^{-8}$ M and reached a maximum effect at $10^{-4}$ M. With a value of 109.3±2.72% and $EC_{50}$ of 4.30×$10^{-9}$ M. Oxime (2) also produced dose-dependent vasodilation in rings without endothelium (E−), reaching an $E_{max}$ of 110.3±4.40%, with a value of $EC_{50}$ of 4.65×$10^{-9}$ M.

The invention claimed is:

1. A method of preparing semi-synthetic oximes, comprising:
    a) applying an extract of *S. nutans* or *X. poposum* plants to a chromatographic column or a thin layer chromatography plate to obtain a metabolite of formula:

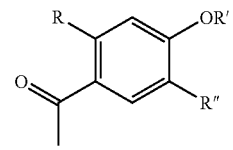

wherein R corresponds to H, OH or methyl; R' and R" corresponds to H, methyl, propyl, propylene, 3-methylbutyl-2-ene, or R' and R" together form a dihydrobenzofuran derivative;
    b) heating under reflux between 100 mg to 400 mg of the metabolite obtained from step a) with a mixture of from 30 to 250 mg of hydroxylamine hydrochloride dissolved in 5 mL of ethanol and from 150-400 pL of pyridine at 40° C.-60° C. for 18-38 hours;
    c) separating the organic phase from the reaction mixture by liquid-liquid extraction using an organic solvent selected from dichloromethane, chloroform, ethyl acetate or ethyl ether;
    d) concentrating the organic phase on a rotary evaporator;
    e) purifying the oxime by silica gel column chromatography, wherein each column progress is monitored by thin layer chromatography.

2. The method according to claim 1, wherein the metabolite obtained in step (a) is Metabolite (A) of formula:

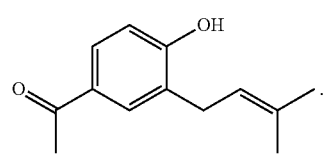
(A)

3. The method according to claim 1, wherein the metabolite obtained in step (a) is Metabolite (B) of formula:

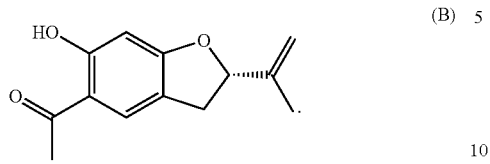

(B)

4. The method according to claim 1, wherein dichloromethane is used as a solvent in step (c).

5. Semi-synthetic oximes derived from metabolites obtained from extracts of medicinal plants according to claim 1, wherein they have the following formula:

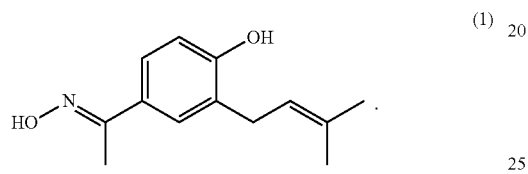

(1)

6. A method for treating vasodilation or hypotension in a subject comprising administering the semi-synthetic oxime according to claim 5.

* * * * *